(12) United States Patent
Emanuel

(10) Patent No.: US 11,471,414 B2
(45) Date of Patent: Oct. 18, 2022

(54) COMPOSITIONS AND METHODS FOR THE TREATMENT AND PROPHYLAXIS OF SURGICAL SITE INFECTIONS

(71) Applicant: Polypid Ltd., Petach-Tikva (IL)

(72) Inventor: Noam Emanuel, Rehovot (IL)

(73) Assignee: POLYPID LTD., Petach-Tikva (IL)

( * ) Notice: Subject to any disclaimer, the term of this patent is extended or adjusted under 35 U.S.C. 154(b) by 0 days.

(21) Appl. No.: 16/790,009

(22) Filed: Feb. 13, 2020

(65) Prior Publication Data

US 2020/0268669 A1 Aug. 27, 2020

Related U.S. Application Data

(63) Continuation of application No. 15/513,164, filed as application No. PCT/IB2015/057409 on Sep. 27, 2015, now abandoned.

(60) Provisional application No. 62/058,809, filed on Oct. 2, 2014.

(51) Int. Cl.
| | |
|---|---|
| A61K 9/16 | (2006.01) |
| A61K 9/00 | (2006.01) |
| A61K 9/14 | (2006.01) |
| A61K 31/65 | (2006.01) |
| A61K 45/06 | (2006.01) |
| A61K 9/70 | (2006.01) |
| A61K 31/575 | (2006.01) |
| A61K 31/685 | (2006.01) |

(52) U.S. Cl.
CPC .......... *A61K 9/1676* (2013.01); *A61K 9/0024* (2013.01); *A61K 9/146* (2013.01); *A61K 9/148* (2013.01); *A61K 9/1611* (2013.01); *A61K 9/1635* (2013.01); *A61K 9/1682* (2013.01); *A61K 9/70* (2013.01); *A61K 31/575* (2013.01); *A61K 31/65* (2013.01); *A61K 31/685* (2013.01); *A61K 45/06* (2013.01)

(58) Field of Classification Search
CPC .... A61K 9/1676; A61K 9/0024; A61K 9/146; A61K 9/148; A61K 9/1611; A61K 9/1635; A61K 9/1682; A61K 9/70; A61K 31/575; A61K 31/65; A61K 31/685; A61K 45/06

See application file for complete search history.

(56) References Cited

U.S. PATENT DOCUMENTS

| | | | | |
|---|---|---|---|---|
| 8,449,916 B1 ‡ | 5/2013 | Bellaire | | A61K 9/14 424/489 |
| 8,877,242 B2 * | 11/2014 | Emanuel | | A61L 27/18 424/486 |
| 8,992,979 B2 * | 3/2015 | Emanuel | | A61K 31/65 424/486 |
| 9,173,976 B2 * | 11/2015 | Emanuel | | A61P 31/04 |
| 9,421,271 B2 * | 8/2016 | Emanuel | | A61L 27/58 |
| 10,105,443 B2 ‡ | 10/2018 | Emanuel | | A61L 27/18 |
| 10,682,412 B2 * | 6/2020 | Emanuel | | A61P 31/00 |
| 2004/0087520 A1 * | 5/2004 | Chowdhury | | A61K 47/10 514/35 |
| 2008/0119494 A1 ‡ | 5/2008 | Young | | A61P 41/00 514/25 |
| 2011/0117197 A1 * | 5/2011 | Emanuel | | A61K 9/0087 424/486 |
| 2011/0294760 A1 ‡ | 12/2011 | Bahulekar | | A61K 9/1647 514/154 |
| 2012/0128622 A1 ‡ | 5/2012 | Berman | | A61K 9/0014 424/78.06 |
| 2016/0354470 A1 ‡ | 12/2016 | Emanuel | | A61L 27/18 |

FOREIGN PATENT DOCUMENTS

| | | | | |
|---|---|---|---|---|
| IL | WO-2010007623 A1 ‡ | 1/2010 | | A61L 27/18 |
| WO | WO-2010007623 A1 ‡ | 1/2010 | | |
| WO | WO-2014020610 A1 ‡ | 2/2014 | | |

OTHER PUBLICATIONS

Fry DE. The prevention of surgical site infection in elective colon surgery. Scientifica (Cairo). 2013;2013:896297. doi:10.1155/2013/896297 (Year: 2013).*

Sica GS, Biancone L. Surgery for inflammatory bowel disease in the era of laparoscopy. World J Gastroenterol. 2013;19(16):2445-2448. doi:10.3748/wjg.v19.i16.2445 (Year: 2013).*

Freeman, Hugh J. "Osteomyelitis and osteonecrosis in inflammatory bowel disease." Canadian Journal of Gastroenterology 11.7 (1997): 601-606. (Year: 1997).*

Emanuel et al., "A lipid-and-polymer-based novel local drug delivery system—bonypidTM: From physicochemical aspects to therapy of bacterially infected bones", Journal of Controlled Release, 160.2: 353-361, Apr. 4, 2012.‡

Tom et al., Ann Thorac Surg, 2009, 88, pp. 695-702.‡

Misra et al., Methods in Enzymology, 509, pp. 61-85. (Year: 2012).‡

The dermatologist, Managing CA-MRSA, obtained online at https://www.the-dermatologist.com/content/managing-ca-mrsa, downloaded on Oct. 16, 2018, pp. 1-7. (Year: 2012).‡

* cited by examiner
‡ imported from a related application

*Primary Examiner* — Abigail Vanhorn

(74) *Attorney, Agent, or Firm* — Greenberg Traurig, LLP

(57) ABSTRACT

The present invention provides methods for preventing, inhibiting or treating a surgical site infection associated with a surgical operation comprising the step of applying to the surgical site a biocompatible, biodegradable substrate being impregnated and/or having its surface coated fully or partially with a matrix composition which provides local controlled and prolonged release of at least one pharmaceutically active agent at the surgical site.

22 Claims, 3 Drawing Sheets

COMPOSITIONS AND METHODS FOR THE TREATMENT AND PROPHYLAXIS OF SURGICAL SITE INFECTIONS

CROSS-REFERENCE TO RELATED APPLICATIONS

This application is a continuation of U.S. patent application No. 15/513,164, filed Mar. 22, 2017, entitled "COMPOSITIONS AND METHODS FOR THE TREATMENT AND PROPHYLAXIS OF SURGICAL SITE INFECTIONS", which is a 371 national stage application of International Application No. PCT/M2015/057409, filed Sep. 27, 2015, which claims the benefit of U.S. Provisional Application No. 62/0588,809, filed Oct. 2, 2014 and entitled "COMPOSITIONS AND METHODS FOR THE TREATMENT AND PROPHYLAXIS OF SURGICAL SITE INFECTIONS", the contents of each of which are incorporated herein by reference.

FIELD OF THE INVENTION

The present invention generally relates to sustained release compositions and uses thereof for the prevention and treatment of surgical site infections.

BACKGROUND OF THE INVENTION

Surgical site infection (SSI), an infection at or near surgical incisions within 30 days of an operative procedure, is a commonly-occurring healthcare-associated infection, accounting for 15% of all nosocomial infections and, among surgical patients, represents the most common nosocomial infection. Increased morbidity and mortality are associated with SSI, ranging from wound discharge associated with superficial skin infection to life-threatening conditions such as severe sepsis. SSIs are responsible for an increased economic burden to healthcare systems, including additional postoperative hospital duration and costs.

The onset of a surgical site infection is caused by contaminants that exist in the operative fields and are resistant to administered antimicrobial agents. In the majority of SSI cases, the pathogen source is the native flora of the patient's skin, mucous membranes, or hollow viscera. When skin is incised, underlying tissue is exposed to overlying endogenous flora. *Staphylococcus aureus* is a commonly-isolated organism in SSI, accounting for 15-20% of SSI occurring in hospital; other organisms regularly isolated from SSIs include gram-negative bacilli, coagulase-negative staphylococci, *Enterococcus* spp., and *Escherichia coli*. Methicillin-resistant *S. aureus* (MRSA) is an increasingly important pathogen that causes more than 50% of *S. aureus* hospital-acquired infections in the US and Europe, and presents challenges to treatment due to multiple antibiotic resistance. Yeast species and viral pathogens also pose a risk.

Surgical site infections present a significant clinical problem in orthopedic surgeries, spinal surgeries, operation of the digestive system, cardiac surgeries, breast operations and many other clinical procedures involving skin incision. For example, a serious complication after cardiac surgery with high morbidity and mortality rates reaching 40% is sternotomy wound site infection (Mediastinitis). Patients with Sternal wound infection require longer hospital stay, repeated surgical interventions, long-term antibiotic treatment, a substantial damage to the quality of life, and great suffering to the patient. The cost of treatment and financial burden in these patients for the health systems is estimated to be 3-time-fold compared to patients undergoing open cardiac surgery, without any developed infection.

Typically colonization of surgical sites with biofilm makes them resistant to both antimicrobial as well as other interventions such as surgical debridement aimed at treating wound infection. Indeed, in recent years, despite the development of new surgical techniques, new antibiotics, new technologies for postoperative infection diagnosis, and wound care technologies, the occurrence of surgical site infections has not been reduced.

International Publication No. WO 2010/007623 to one of the inventors of the present invention and others, the contents of which are incorporated herein by reference, discloses drug delivery compositions for controlled release of an active ingredient, comprising a lipid-based matrix with a biodegradable polymer. These drug delivery compositions enable to entrap a large variety of one or more biologically active molecules and to release them at a pre-programmed rate for periods ranging from several days to several months.

International Publication No. WO2014/020610 to the inventor of the present invention, the contents of which are incorporated herein by reference, discloses compositions, methods and medical devices for the treatment of bone voids and bone defects comprising the step of applying to a bone void or bone defect site a composition comprising a matrix which provides local prolonged release of at least one antibiotic agent at the bone void site.

Surgical site infections are still a major problem of the health care system. There is a need in the field for treatments to prevent and treat surgical site infections locally at the surgical site.

SUMMARY OF THE INVENTION

The present invention provides methods for preventing, inhibiting or treating a surgical site infection associated with a surgical operation comprising the step of applying to the surgical site a biocompatible, biodegradable substrate being impregnated and/or having its surface coated fully or partially with a matrix composition which provides local controlled and prolonged release of at least one pharmaceutically active agent at the surgical site. Specifically, the matrix composition comprises (a) a biocompatible polymer, (b) a first lipid component comprising a sterol, (c) a second lipid component comprising at least one phospholipid having fatty acid moieties of at least 12 carbons; and (d) a pharmaceutically active agent selected from the group consisting of an antibiotic agent, antiseptic agent, an anti-inflammatory agent, anti-fungal agent and any combination thereof.

The substrate being impregnated and/or having its surface coated fully or partially with a matrix composition described herein is intended for local administration to soft tissues and solid organs during surgical procedures and provides localized infection prevention and treatment by reducing the overall infection rate post-surgery and by reducing or eradicating soft tissue infections that may exist prior to surgery. According to some embodiments, the drug coated substrate described herein prevents or inhibits the formation of biofilm that may form at the surgical site and its vicinity, thereby preventing or inhibiting surgical site infections. Inhibition of biofilm formation at the surgical site refers to inhibition of biofilm formation on surfaces such as biological tissues and/or materials or devices that may be used during surgery (e.g. wound tissue, necrotic cells, biomaterials and surgical implants (e.g. sutures and hard ware-stainless steel wires)). According to some embodiments, the drug coated substrate disclosed herein is capable of eradicating an existing biofilm.

Following its application to the surgical site, the substrate being impregnated and/or having its surface coated fully or partially with a matrix composition described herein provides local controlled release of the drug at the surgical site and its surrounding over a predetermined, prolonged period of time, preferably between several days to several weeks, thereby preventing or eradicating tissue infection.

The substrate impregnated or coated fully or partially with the matrix composition according to some embodiments of the invention, is preferably administered to a subject that has or is at risk of developing an infection, prior to or during a treatment of the subject with a process that may cause infection and/or the formation of a biofilm in the subject. According to some embodiments, such process may be any surgical procedure such as orthopedic surgical operations (e.g. hip arthroplasty, knee arthroplasty, total joint replacement, trauma), spine surgical operations, surgical operations on a digestive system organ (e.g. esophagus, stomach, small intestine, large intestine, rectum, colon, appendix, liver, pancreas, gallbladder, gastric ulcer, gastric cancer procedures, open gastric bypass, appendectomy, colectomy, cholecystectomy, vagotomy, open billary tract procedures, small intestine procedures, colorectal procedures), cardiac procedures (e.g. coronary artery bypass, cardiothoracic transplantation procedures, cardiac device insertion procedures), hernia repair, vascular procedures, caesarian, prostatectomy, obstetric and gynecologic surgical operations (e.g. hysterectomy), head and neck cancer surgery, transplantation surgeries (e.g. lung, liver, pancreas, kidney), neurosurgery (e.g. deep brain stimulation implant) and plastic surgeries (e.g. breast reconstruction, mastectomy).

The methods for preventing or inhibiting surgical site infections are useful for preventing or inhibiting postoperative infection in contaminated or potentially contaminated surgery, wherein the postoperative infection may be any one of a superficial incisional infection, a deep incisional infection and an organ/space infection. Also disclosed are methods for treating surgical site infections including preoperative, intraoperative and/or postoperative infections. Said pre-operative and/or postoperative infections may be associated with biofilm formation. Pre-operative infection may involve a biofilm formed in connection with a disease or condition in an organ, tissue or body system (e.g. bone, skin, abdomen, urinary tract etc.). Such disease or condition may be selected, for example, from medical device related infections, orthopedic implant infection, biliary stents and catheter-related infections.

The method for suppressing, preventing and the method for treating surgical site infection according to embodiments of the invention, may be additional to standard procedures for reduction in the inoculum of bacteria such as appropriate surgical site preparation, systemic preventive antibiotics, cell based therapy, and enhancement of the host by perioperative supplemental oxygenation, maintenance of normothermia and glycemic control.

According to some embodiments, the present invention provides a substrate being impregnated or having its surface coated fully or partially with a matrix composition comprising (a) a biocompatible polymer, (b) a first lipid component comprising a sterol which is non-covalently associated with the biocompatible polymer, (c) a second lipid component comprising at least one phospholipid having fatty acid moieties of at least 12 carbons; and (d) at least one of an antibiotic agent, an antiseptic agent, an anti-inflammatory agent, an anti-fungal agent or any combination thereof, said coated substrate is suitable for local administration to a surgical site and is capable of preventing or treating surgical site infections. According to some embodiments, the matrix compositions provide sustained release of the pharmaceutically active agent at the surgical site.

According to some embodiments, the substrate used in compositions and methods described herein is a bioabsorbable hydrophilic material, which has biocompatibility (that is, is low in toxicity, shows only low foreign body reactions in the living body, and may have a good affinity with the body tissue), bioabsorbability (that is, biodegradability), and hydrophilicity, but which has low solubility in water or is insoluble in water, and further has a solid shape at ambient temperature and formability. Any materials having these properties may be used without limitation. The bioabsorbable hydrophilic materials according to some embodiments of the invention include mineral substrates, natural polymeric substrates and synthetic derivatives thereof. Non-limiting examples of mineral substrates include hydroxyapatite, fluorapatite, oxyapatite, wollastonite, apatite/wollastonite glass ceramics, anorthite, calcium fluoride, calcium sulfate, calcium carbonate, tetracalcium phosphate, α-tricalcium phosphate (α-TCP), β-tricalcium phosphate (β-TCP), amorphous calcium phosphate, dicalcium phosphate, agrellite, devitrite, canasite, phlogopite, monetite, brushite, octocalcium phosphate, whitlockite, cordierite, berlinite, combeite, phosphoric acid crystals, disodium hydrogen phosphate, and other phosphate salt-based bioceramics. Non-limiting examples of natural polymeric substrates include gelatin, hyaluronic acid, hyaluronic acid derivatives, such as, a polyionic complex of hyaluronic acid, triethanolamine alginate, casein, keratin, myosin and/or fibroin, collagen, collagen derivatives, such as, succinylated collagen or methylated collagen, chondrotin sulfate, chitosan, chitosan derivatives, such as, methylpyrrolidone-chitosan, polyaminogalactosamine. According to some embodiments, the substrate is a water-soluble synthetic polymer such as for example poly vinyl alcohol (PVA), poly vinyl pyrrolidone (PVP), poly acrylic acid (PAA), N-(2-Hydroxypropyl) methacrylamide (HPMA), Poly(2-alkyl-2-oxazolines), polyphosphoesters (PPE), polyphosphates, and polyphosphonates. According to certain embodiments, the substrate is poly vinyl alcohol (PVA). According to some embodiments, the substrate is a bioabsorbable hydrophobic material, such as for example a biodegradable polyester selected from the group consisting of PLA (polylactic acid), PGA (poly glycolic acid), PLGA (poly (lactic-co-glycolic acid)) and combinations thereof.

In some embodiments, the substrate is dense. In some embodiments, the substrate is porous. In some embodiments, the substrate is shaped in the form of particles (or granules). The substrate particles are typically spherical or steroidal. In some embodiments, the substrate particles, which need not be spherical and/or steroidal but preferably are spherical and/or spheroidal, may have an average diameter of for example at least about 30 μm, at least about 40 μm, at least about 50 μm, at least about 60 μm, at least about 70 μm, at least about 80 μm, at least about 90 μm, at least about 100 μm, between 50 μm and 200 μm, between 50 μm and 180 μm, between 70 μm and 150 μm and between 80 μm and 120 μm, between 50 μm and 100 μm and between 70 μm and 100 μm, not more than about 500 μm, not more than about 400 rpm, not more than about 350 μm, not more than about 300 μm, not more than about 250 μm, not more than about 200 rpm, not more than about 180 rpm, not more than about 150 μm, not more than about 140 μm, not more than about 130 µm, not more than about 120 µm, not more than about 110 µm, not more than about 100 µm. According to some embodiments, the substrate particles are in the form of a powder. According to some embodiments, the substrate may be of any shape (e.g. a sponge, net, sheet or fiber). It is appreciated by the one skilled in the art, that the shape and/or size of the substrate may be adjusted, before or after coating or impregnating with the matrix composition, according to need (e.g. type, size and location of incision). Each possibility represents a separate embodiment of the invention.

In some embodiments, the biocompatible polymer in the coating matrix composition comprises a polyester selected from the group consisting of PLA (polylactic acid), PGA (poly glycolic acid), PLGA (poly (lactic-co-glycolic acid)) and combinations thereof. According to some embodiments, the biocompatible polymer constitutes 5-30% of the matrix. According to some embodiments, the biocompatible polymer is polyethylene glycol (PEG), preferably PEG having molecular weight of up to 10,000 Dalton inclusive.

According to particular embodiments the first lipid comprises at least one sterol. In some embodiments, the sterol is a phytosterol. In some embodiments, the sterol is a zoosterol. According to specific embodiments, the sterol is a cholesterol. In some embodiments, the first lipid component comprises a mixture of sterols. In some embodiments, the first lipid component is substantially free of non-sterol lipids. In some embodiments, the first lipid component constitutes 5-40% (w/w) of the matrix. In some preferred embodiments, the sterol is cholesterol and constitutes up to 50% (w/w) of the total lipid content of said matrix composition. Total lipid content refers to total mass of all the lipids in the matrix composition. for example, first lipid component, second lipid component and any additional lipid additive comprised in the matrix composition. According to particular embodiments the first lipid and polymer are non-covalently associated.

In some embodiments, the fatty acid chains of the phospholipid contains at least 12 carbon atoms each. In some embodiments, the fatty acid chains of the phospholipid contains no more than 18 carbon atoms each. In some embodiments, the fatty acid chains of the phospholipid are fully saturated. In some embodiments, at least one of the phospholipid fatty acid chains is non-saturated (e.g. contains at least one double bond). In some embodiments, both phospholipid fatty acid chains are non-saturated. In some embodiments the second lipid comprises a phospholipid selected from the group consisting of a phosphatidylcholine, a mixture of phosphatidylcholines, a phosphatidylethanolamine, and combinations thereof. According to some embodiments the second lipid comprises a mixture of phosphatidylcholines. According to some embodiments the second lipid component further comprises an additional phospholipid selected from the group consisting of a phosphatidylserine, a phosphatidylglycerol, and a phosphatidylinositol. In some embodiments, the second lipid component constitutes 30-80% (w/w) of the matrix composition.

In some embodiments, the pharmaceutically active agent is incorporated into the matrix composition. According to certain embodiments, the pharmaceutically active agent is an antibiotic agent. According to certain embodiments, the pharmaceutically active agent is an antiseptic agent. According to certain embodiments, the pharmaceutically active agent is an anti-inflammatory agent. According to certain embodiments, the pharmaceutically active agent is a steroid or a non-steroidal anti-inflammatory drug.

According to some embodiments, the pharmaceutically active agent constitutes 1-20% (w/w) of the matrix composition. According to some embodiments, the pharmaceutically active agent constitutes about 5-15% (w/w) of the matrix composition. According to certain typical embodiments, the pharmaceutically active agent constitutes about 8-12% (w/w) of the matrix composition.

According to some embodiments, the coated substrate used for preventing and/or treating surgical site infections constitutes between about 60-90% (w/w) of substrate and 10-40% (w/w) of the matrix composition described herein. According to some embodiments the coated substrate constitutes between about 70-90% (w/w) of substrate and 10-30% (w/w) of the matrix composition. According to some embodiments the coated substrate constitutes between about 80-90% (w/w) of substrate and 10-20% (w/w) of the matrix composition. According to some embodiments the coated substrate constitutes between about 85-90% (w/w) of substrate and 10-15% (w/w) of the matrix composition.

In some embodiments, the coating matrix composition has a highly organized multilayer structure in which the polymer and lipids are organized in the form of multiple alternating layers. According to some embodiments, the matrix composition comprises a continuous structure devoid of internal gaps and/or free volume. According to some embodiments, the matrix composition is lipid saturated indicating that the space between the polymer layers or polymer backbone is filled with lipid molecules in combination the pharmaceutical agent, to the extent that additional lipid moieties can no longer be incorporated into the matrix to an appreciable extent.

In some embodiments, the matrix composition is capable of releasing at least 30% of the pharmaceutical agent at zero-order kinetics. Without being limited by a specific theory or mechanism of action it is suggested that this organized structure or substructure of the matrix composition of the invention is one of the main reasons for the zero-order release rate of the drug or drugs from the matrix formulation following its hydration. Thus, the zero-order release rate may be attributed to slow and continuous "peeling" of drug together with the formulation components from the hydrated surface layer(s) of the highly organized layers of lipids and polymer. According to some embodiments the matrix of the present invention is water resistant. As such water cannot easily, if at all, diffuse into the matrix and the pharmaceutically active agent entrapped between the layers cannot easily, if at all, diffuse out of the matrix. According to some embodiments, the drug is being released from the matrix compositions disclosed herein upon the gradual surface degradation of the matrix, thus enabling extended release ranging from several days to several weeks. The biocompatible substrate itself preserves its three dimensional structure over the course of pharmaceutical agent release due to the hydrophobic matrix composition that coats or impregnates the substrate. Gradual degradation of the matrix composition which will eventually lead to exposure of the substrate's surface. Exposure of the biodegradable substrate to body fluids will initiate its degradation and removal, leaving no traces at the treated surgical site. In a particular embodiment, the present invention provides methods for suppressing, preventing or treating a surgical site infection associated with a surgical operation comprising the step of applying to the surgical site a biodegradable substrate being impregnated and/or having its surface coated fully or partially with a matrix composition comprising: (a) biodegradable polyester; (b) a sterol; (c) a phosphatidylcholine having fatty acid moieties of at least 14 carbons; and (d) an antibiotic agent. In another embodiment, the matrix composition comprises at least 50% lipid by weight of the matrix. In another embodiment, matrix composition comprises at least 40% phospholipids by weight of the matrix. In some embodiments, the biodegradable, slow release coating formulation comprises at least 10% polymer by weight of the matrix. In some embodiments, the biodegradable, slow release coating formulation (matrix) comprises at least 5% antibiotic by weight of the matrix. In another embodiment, the matrix composition is homogeneous. In some embodiments, the polymer, sterol non-covalently associated therewith, and the phospholipid form a structurally ordered lipid-saturated matrix composition that is substantially free of water. According to certain embodiments, the substrate coated/impregnated with the matrix composition is selected from tri-calcium phosphate particles or polyvinyl alcohol particles.

According to some embodiments, the matrix composition comprises: (a) a biodegradable polyester selected from PLA, PGA and PLGA; (b) cholesterol which is non-covalently associated with the biodegradable polyester; (c) at least one phospholipid having fatty acid moieties of 16-18 carbons; and (d) an antibiotic agent. In another embodiment, the matrix composition comprises at least 50% lipid by weight of the matrix. In another embodiment, matrix composition comprises at least 40% phospholipids by weight of the matrix. In some embodiments, the biodegradable, slow release coating formulation comprises at least 10% polymer by weight of the matrix. In some embodiments, the biodegradable, slow release coating formulation (matrix) comprises at least 5% antibiotic by weight of the matrix. In some embodiments, the phospholipid is a phosphatidylcholine. In some embodiments, the phosphatidylcholine is a mixture of phosphatidylcholines. In some embodiments the phosphatidylcholine(s) have saturated fatty acid moieties, i.e. no carbon-carbon double bonds in the fatty acid chains. In some embodiments, the phospholipid is selected from the group consisting of DMPC, DPPC, DSPC, DOPC and any combination thereof. In some embodiments, the phospholipid is selected from DPPC, DSPC and any combination thereof. In some embodiments, the phospholipid is selected from DMPC, DPPC and any combination thereof. In some embodiments, the phospholipid is selected from DMPC, DPPC, DOPC and any combination thereof. In some embodiments, the polymer, cholesterol associated therewith, and the phospholipid form a structurally ordered lipid-saturated matrix composition that is substantially free of water. According to certain embodiments, the substrate coated/impregnated with the matrix composition is selected from tri-calcium phosphate particles or polyvinyl alcohol particles.

According to some embodiments, the matrix composition comprises: (a) Poly ethylene glycol (PEG); (b) cholesterol which is non-covalently associated with the polymer; (c) at least one phospholipid having fatty acid moieties of 14-18 carbons; and (d) an antibiotic agent. In another embodiment, the matrix composition comprises at least 50% lipid by weight of the matrix. In another embodiment, matrix composition comprises at least 40% phospholipids by weight of the matrix. In some embodiments, the biodegradable, slow release coating formulation comprises at least 10% polymer by weight of the matrix. In some embodiments, the biodegradable, slow release coating formulation (matrix) comprises at least 5% antibiotic by weight of the matrix. In some embodiments, the phospholipid is a phosphatidylcholine. In some embodiments, the phosphatidylcholine is a mixture of phosphatidylcholines. In some embodiments the phosphatidylcholine(s) have saturated fatty acid moieties, i.e. no carbon-carbon double bonds in the fatty acid chains. In some embodiments, the phospholipid is selected from the group consisting of DMPC, DPPC, DSPC, DOPC and any combination thereof. In some embodiments, the phospholipid is selected from DPPC, DSPC and any combination thereof. In some embodiments, the phospholipid is selected from DMPC, DPPC and any combination thereof. In some embodiments, the phospholipid is selected from DMPC, DPPC, DOPC and any combination thereof. In some embodiments, the polymer, cholesterol associated therewith, and the phospholipid form a structurally ordered lipid-saturated matrix composition that is substantially free of water. According to certain embodiments, the substrate coated/impregnated with the matrix composition is selected from tri-calcium phosphate particles or polyvinyl alcohol particles.

The present invention provides a biodegradable substrate which is impregnated and/or which has its surface coated fully or partially with a matrix composition which provides local controlled and prolonged release of at least one pharmaceutically active agent for use in suppressing or preventing a surgical site infection associated with a surgical operation. Specifically, the coating matrix composition comprises (a) a biocompatible polymer, (b) a first lipid component comprising a sterol, (c) a second lipid component comprising at least one phospholipid having fatty acid moieties of at least 12 carbons; and (d) a pharmaceutically active agent.

The present invention further provides a biodegradable substrate which is impregnated and/or which has its surface coated fully or partially with a matrix composition which provides local controlled and prolonged release of at least one pharmaceutically active agent for use in treating surgical site infection associated with a surgical operation. Specifically, the coating matrix composition comprises (a) a biocompatible polymer, (b) a first lipid component comprising a sterol, (c) a second lipid component comprising at least one phospholipid having fatty acid moieties of at least 12 carbons; and (d) a pharmaceutically active agent.

The present invention further provides a biodegradable substrate which is impregnated and/or which has its surface coated fully or partially with a matrix composition comprising (a) a biocompatible polymer, (b) a first lipid component comprising a sterol, (c) a second lipid component comprising at least one phospholipid having fatty acid moieties of at least 12 carbons; and (d) a pharmaceutically active agent, for use in administering said pharmaceutically active agent to soft tissues and solid organs during surgical procedures of a subject in need thereof.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 3C and 3D show that both outer and inner surfaces of the particles are coated.

DETAILED DESCRIPTION OF THE INVENTION

Figure 1:
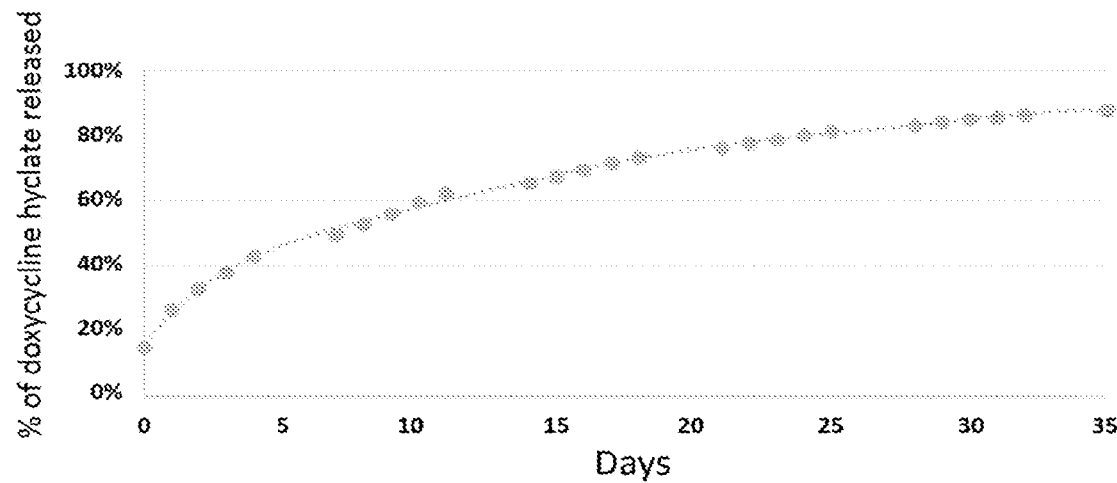
FIG. 1 shows the accumulated release profile of doxycycline hyclate from hydrated (5% serum at 37° C.) tri-calcium phosphate (TCP) particles (~100 μm) impregnated with a matrix composition composed of PLGA, cholesterol, DPPC, DSPC and doxycycline hyclate.

The present invention provides methods for preventing or treating a surgical site infection associated with a surgical operation comprising the step of applying to the surgical site a biocompatible, biodegradable substrate being impregnated and/or having its surface coated fully or partially with a matrix composition which provides local controlled and prolonged release of at least one pharmaceutically active agent at the surgical site of a subject in need thereof. Specifically, the matrix composition comprises (a) a biocompatible polymer, (b) a first lipid component comprising a sterol, (c) a second lipid component comprising at least one phospholipid having fatty acid moieties of at least 12 carbons; and (d) a pharmaceutically active agent selected from the group consisting of an antibiotic agent, antiseptic agent, an anti-inflammatory agent, anti-fungal agent and any combination thereof.

As used herein, the term "surgical site" refers to a site created by any opening in the skin or internal organs performed for a specific medical purpose. A surgical site being "open" refers to surgical sites where medical personnel have direct physical access to the area of interest. A surgical site may include, but is not limited to, organs, muscles, tendons, ligaments, connective tissue and the like.

The methods of the present invention are also suitable for the treatment of open wounds. Open wounds as used herein refer generally to a bodily injury with disruption of the normal integrity of tissue structures and more particularly to a type of injury in which skin is torn, cut, or punctured. Open wounds include without limitation: Incisions or incised wounds, lacerations, penetration wounds, septic wounds, burn injuries etc.

As used herein, "preventing" or "prophylaxis" of surgical site infection relate to inhibiting or eradicating the replication of bacteria at the surgical site and its surroundings, inhibit transmission of bacteria or preventing the bacteria from establishing itself at the surgical site and its surroundings, or alleviating the symptoms of a disease that may be caused by infection. A treatment will be considered therapeutic if there is a reduction in bacterial load.

The methods according to some embodiments of the invention are suitable for the prevention or inhibition of biofilm formation at the surgical site and its vicinity in a subject in need thereof. Inhibition of biofilm formation at the surgical site refers to inhibition of biofilm formation on surfaces such as biological tissues and/or materials or devices that may be used or implanted during surgery. According to some embodiments, the drug coated substrate disclosed herein is also capable of eradicating an existing biofilm formed prior to the surgical operation.

The term "biofilm" is defined herein in accordance with its regular meaning in the art as a structured community of microorganisms growing attached to a surface and producing a slime layer of extracellular polymers in which the microbial consortia is embedded in a protective environment. The surfaces to which the biofilm is adherent to may be inert or living surfaces (e.g. wound tissue, necrotic cells, biomaterials and surgical implants (e.g. sutures and hardware-stainless steel wires)). A biofilm community can include bacteria, fungi, yeasts protozoa and other microorganisms. Biofilms that are commonly found associated with human tissue and organ surfaces are frequently bacterial biofilms.

The "subject" as used herein refers to an individual, a patient, that has infection, is developing an infection (biofilm formation is clinically evident or detectable to the skilled artisan, but has not yet fully formed), or is at risk of developing an invention (no biofilm formation is yet detectable to the clinician or skilled artisan, but the subject is known to be at risk of developing a biofilm due to disease or the pending performance of a surgical procedure, such as for example a cardiac surgery or graft implantation). The term "subject" refers to a mammal, preferably a human that is to be treated or is being treated by a clinician (doctor, nurse or other medical practitioner) for a disease, condition, procedure, or routine examination.

The term "controlled release" refers to control of the rate and/or quantity of pharmaceutically active agent(s) delivered by the matrix compositions of the invention. The controlled release can be continuous or discontinuous, and/or linear or non-linear.

The term "sustained release" means that pharmaceutical active agent is released over an extended period of time.

General Characteristics of the Matrix Composition Used for Substrate Coating

The matrix composition used for impregnating or coating a biodegradable substrate according to some embodiments of the invention comprises (a) a biocompatible polymer, (b) a first lipid component comprising at least one sterol which is non-covalently associated with the biocompatible polymer (c) a second lipid component comprising at least one phospholipid having fatty acid moieties of at least 12 carbons; and (d) a pharmaceutically active agent. The matrix compositions provide sustained release of the pharmaceutically active agent at a surgical site in the body of a subject in need thereof.

In specific embodiments, the polymer and the lipids form a structurally ordered lipid saturated matrix composition that is substantially free of water. In some embodiments, the matrix composition has a highly organized multilayer structure in which the polymer and lipids are organized in the form of multiple alternating layers. In some embodiments, the biocompatible coating matrix comprises at least about 50% total lipids by weight.

In some embodiments, the matrix composition comprises at least 10% biocompatible polymer by weight. In some embodiments, the matrix composition comprises between about 10-30% polymer by weight. In some embodiments, the matrix composition comprises between about 15-25% polymer by weight. In some embodiments the matrix composition comprises about 20% polymer by weight. In some embodiments the biocompatible polymer constitutes at least 10% (w/w), at least 11% (w/w), at least 12% (w/w), at least 13% (w/w), at least 14% (w/w), at least 15% (w/w), at least 16% (w/w), at least 17% (w/w), at least 18% (w/w), at least 19% (w/w), at least 20% (w/w), at least 21% (w/w), at least 22% (w/w), at least 23% (w/w), at least 24% (w/w), at least 25% (w/w), at least 26% (w/w), at least 27% (w/w), at least 28% (w/w), at least 29% (w/w), at least 30% (w/w) of the matrix.

According to certain embodiments of the invention, the polymer is a biodegradable polyester. According to some embodiments the polyester is selected from the group consisting of PLA (polylactic acid). "PLA" refers to poly(L-lactide), (poly(D-lactide), and (poly(DL-lactide). In another embodiment, the polymer is PGA (polyglycolic acid). In another embodiment, the polymer is PLGA (poly(lactic-co-glycolic acid). The PLA contained in the PLGA may be any PLA known in the art, e.g. either enantiomer or a racemic mixture. The PLGA of methods and compositions of the present invention has, in another embodiment, a 50:50 lactic acid/glycolic acid ratio. In another embodiment, the ratio is 60:40. In another embodiment, the ratio is 75:25. In another embodiment, the ratio is 85:15. In another embodiment, the ratio is 90:10. In another embodiment, the ratio is 95:5. In another embodiment, the ratio is another ratio appropriate for an extended or sustained in vivo release profile. The PLGA may be either a random or block copolymer. Each possibility represents a separate embodiment of the present invention. It is to be emphasized that the polymer may be of any size or length (i.e of any molecular weight).

In another embodiment, the biodegradable polyester may be selected from the group consisting of polycaprolactone, polyhydroxyalkanoate, polypropylenefumarate, polyorthoester, polyanhydride, and polyalkylcyanoacrylate, provided that the polyester contains a hydrogen bond acceptor moiety. In another embodiment, the biodegradable polyester is a block copolymer containing a combination of any two monomers selected from the group consisting of a PLA, PGA, a PLGA, polycaprolactone, a polyhydroxyalkanoate, a polypropylenefumarate, a polyorthoester, a polyanhydride, and a polyalkylcyanoacrylate. In another embodiment, the biodegradable polyester is a random copolymer containing a combination of any two of the monomers listed above. Each possibility represents a separate embodiment of the present invention.

The term "biodegradable" refers to a substance that will degrade over time by hydrolytic action, by the action of enzymes and/or by other similar mechanisms in the human body. "Biodegradable" further includes that a substance can break down or degrade within the body to non-toxic components after or while a therapeutic agent has been or is being released.

The term "Biocompatible" refers to a substance that will not cause substantial tissue irritation or necrosis at the target tissue site.

According to some embodiments, the matrix composition comprises up to 40% (w/w) of a first lipid component comprising a sterol which is non-covalently associated with the biocompatible polymer. According to some embodiments, the sterol constitutes up to about 30% (w/w) of the weight of the matrix composition. According to some embodiments, the matrix composition comprises about 5-40% (w/w) of a first lipid component comprising a sterol. According to some embodiments, the matrix composition comprises about 5-30% (w/w) of sterol. According to some embodiments, the matrix composition comprises about 5-20% (w/w) of sterol. According to some embodiments, the matrix composition comprises about 5-15% (w/w) of sterol. According to some embodiments, the matrix composition comprises about 7-13% (w/w) of sterol. According to some embodiments, the matrix composition comprises about 9-11% (w/w) of sterol. According to certain typical embodiments, the matrix composition comprises about 10% (w/w) of sterol. In some embodiments the sterol constitutes at least 5% (w/w), at least 6% (w/w), at least 7% (w/w), at least 8% (w/w), at least 9% (w/w), at least 10% (w/w), at least 11% (w/w), at least 12% (w/w), at least 13% (w/w), at least 14% (w/w), at least 15% (w/w), at least 16% (w/w), at least 17% (w/w), at least 18% (w/w), or at least 19% (w/w) of the matrix. In some embodiments, sterol constitutes not more than 20% (w/w), not more than 19% (w/w), not more than 18% (w/w), not more than 17% (w/w), not more than 16% (w/w), not more than 15% (w/w), not more than 14% (w/w), not more than 13% (w/w), not more than 12% (w/w), not more than 11% (w/w), not more than 10% (w/w), not more than 9% (w/w), not more than 8% (w/w), not more than 7% (w/w), not more than 6% (w/w), or not more than 5% (w/w) of the matrix. According to some currently preferred embodiments, the sterol is cholesterol.

According to some embodiments, the matrix composition comprises at least about 30% (w/w) of a second lipid component comprising at least one phospholipid having fatty acid moieties of at least 12 carbons. According to some embodiments, the matrix composition comprises at least about 40% (w/w) of a second lipid component comprising at least one phospholipid having fatty acid moieties of at least 12 carbons. According to some embodiments, the matrix composition comprises about 40-75% (w/w) of a second lipid component comprising at least one phospholipid having fatty acid moieties of at least 12 carbons. According to some embodiments, the matrix composition comprises about 50-70% (w/w) of a second lipid component comprising at least one phospholipid having fatty acid moieties of at least 12 carbons. According to certain typical embodiments, the matrix composition comprises about 60% (w/w) a second lipid component comprising at least one phospholipid having fatty acid moieties of at least 12 carbons. In some embodiments, the second lipid component comprising at least one phospholipid having fatty acid moieties of at least 12 carbons constitute at least 40% (w/w), at least 45% (w/w), at least 50% (w/w), at least 55% (w/w), at least 60% (w/w), at least 65% (w/w), or at least 70% (w/w), of the matrix. In some embodiments, the second lipid component comprising at least one phospholipid having fatty acid moieties of at least 12 carbons constitute not more than 75% (w/w), not more than 70% (w/w), not more than 65% (w/w) of the matrix. According to some embodiments, the second lipid component comprises at least one phospholipid molecule having fatty acid moieties of at least 14 carbons. According to some embodiments, the second lipid component comprises at least one phosphatidylcholine molecules having fatty acid moieties of at least 14 carbons. According to some embodiments, the phosphatidylcholine molecules of the composition comprise DMPC. According to some embodiments, the phosphatidylcholine molecules of the composition comprise DPPC. According to some embodiments, the phosphatidylcholine molecules of the composition comprise DSPC. According to some embodiments, the matrix composition comprises DOPC. According to some embodiments, the matrix composition comprises a mixture of DOPC with a second phospholipid having fatty acid moieties of at least 14 carbons. According to some embodiments, the matrix composition comprises a mixture of DMPC and DPPC. Typically the ratio between DMPC and DPPC in the formulation is between about 10:1 to 1:10. According to some embodiments, the matrix composition comprises a mixture of DPPC and DSPC. Typically the ratio between DPPC and DSPC in the formulation is between about 10:1 to 1:1; preferably between 5:1 and 2:1; more preferably the ratio between DPPC and DSPC in the formulation is about 3:1. According to some embodiments, the matrix composition comprises about 50-70% (w/w) of a mixture of DMPC and DPPC. According to some embodiments, the matrix composition comprises about 50-70% (w/w) of a mixture of DPPC and DSPC.

In some embodiments, the lipid:polymer weight ratio of a composition of the present invention is between 1:1 and 9:1 inclusive. In another embodiment, the ratio is between 2:1 and 9:1 inclusive. In another embodiment, the ratio is between 3:1 and 9:1 inclusive. In another embodiment, the ratio is between 4:1 and 9:1 inclusive. In another embodiment, the ratio is between 5:1 and 9:1 inclusive. In another embodiment, the ratio is between 6:1 and 9:1 inclusive. In another embodiment, the ratio is between 7:1 and 9:1 inclusive. In another embodiment, the ratio is between 8:1 and 9:1 inclusive. In another embodiment, the ratio is between 1.5:1 and 9:1 inclusive. Each possibility represents a separate embodiment of the present invention.

It is to be emphasized that the sustained release period using the compositions of the present invention can be programmed taking into account the biochemical and/or biophysical properties of the biopolymer and the lipid. Specifically, the degradation rate of the polymer and the fluidity of the lipid should be considered. For example, a PLGA (85:15) polymer will degrade slower than a PLGA (50:50) polymer. A phosphatidylcholine (12:0) is more fluid (less rigid and less ordered) at body temperature than a phosphatidylcholine (18:0). Thus, for example, the release rate of a drug incorporated in a matrix composition comprising PLGA (85:15) and phosphatidylcholine (18:0) will be slower than that of a drug incorporated in a matrix composed of PLGA (50:50) and phosphatidylcholine (14:0). Another aspect that will determine the release rate is the physical characteristics of the entrapped or impregnated drug. In addition, the release rate of drugs can further be controlled by the addition of other lipids into the matrix formulation, some of which are described below.

According to some embodiments, the matrix composition comprises about 1-20% (w/w) of the pharmaceutically active agent. According to some embodiments, the matrix composition comprises about 5-15% (w/w) of the pharmaceutically active agent. According to certain embodiments, the matrix composition comprises about 8-12% (w/w) of the pharmaceutically active agent. According to certain embodiments, the matrix composition comprises about 10% (w/w) of the pharmaceutically active agent. In some embodiments, the pharmaceutically active agent constitutes at least 1% (w/w), at least 2% (w/w), at least 3% (w/w), at least 4% (w/w), at least 5% (w/w), at least 6% (w/w), at least 7% (w/w), at least 8% (w/w), at least 9% (w/w), at least 10% (w/w), at least 11% (w/w), at least 12% (w/w), at least 13% (w/w), at least 14% (w/w), at least 15% (w/w), at least 16% (w/w), at least 17% (w/w), at least 18% (w/w), or at least 19% (w/w) of the matrix. In some embodiments, the pharmaceutically active agent constitutes not more than 20% (w/w), not more than 19% (w/w), not more than 18% (w/w), not more than 17% (w/w), not more than 16% (w/w), not more than 15% (w/w), not more than 14% (w/w), not more than 13% (w/w), not more than 12% (w/w), not more than 11% (w/w), not more than 10% (w/w), not more than 9% (w/w), not more than 8% (w/w), not more than 7% (w/w), not more than 6 (w/w), not more than 5% (w/w) of the matrix.

According to certain embodiments, the pharmaceutically active agent is an antibiotic agent. According to certain embodiments, the pharmaceutically active agent is an antifungal agent. According to certain embodiments, the pharmaceutically active agent is an antiseptic agent. According to certain embodiments, the pharmaceutically active agent is an anti-inflammatory agent. According to certain embodiments, the pharmaceutically active agent is a steroid or a non-steroidal anti-inflammatory drug. In some embodiment, a plurality of pharmaceutically active agents are incorporated into the matrix composition, for example, a combination of two or more antibiotic agents, a combination of one or more antibiotic agents and one or more antifungal agent, a combination of one or more antibiotic agents and one or more non-steroidal anti-inflammatory drugs (NSAID). In some embodiments, the pharmaceutically active agent is incorporated into the matrix composition. Each possibility represents a separate embodiment of the present invention. According to some embodiments, the pharmaceutically active agent has low water solubility. In another embodiment, the pharmaceutically active agent is hydrophobic. In another embodiment, the pharmaceutically active agent is an amphipathic.

The term "hydrophobic" relates to a material, having solubility in distilled water at ambient temperature of less than about 1 gr per 100 ml, or less than about 0.5 gm per 100 ml, or less than about 0.1 gm per 100 ml.

A pharmaceutically active agent having low water solubility as used herein, relates to a material having solubility in distilled water at ambient temperatures of less than about 3 gr per 100 ml, or less than about 2 gr per 100 ml, between 1-2 gr per 100 ml.

According to some embodiments, the pharmaceutically active agent used in methods according to some embodiments of the invention is an antibiotic agent selected from the group consisting of penicillin antibiotics, cephem antibiotics, macrolide antibiotics, tetracycline antibiotics, glycycycline antibiotics, fosfomycin antibiotics, aminoglyco side antibiotics, and new quinolone antibiotics. Non-limiting examples of antibiotic agents include amoxicillin, amoxicillin/clavulanic acid, ampicillin/sulbactam, penicillin, metronidazole, clindamycine, chlortetracycline, dcmeclocycline, oxytetracycline, amikacin, gentamicin, kanamycin, neomycin, netilmicin, streptomycin, tobramycin, cefadroxil, cefazolin, cephalexin, cephalothin, cephapirin, cephradine, cefaclor, cefamandole, cefametazole, cefonicid, cefotetan, cefoxitine, cefpodoxime, cefprozil, cefuroxime, cefdinir, cefixime, cefoperazone, cefotaxime, ceftazidime, ceftibuten, ceftizoxime, ceftriaxone, cefepime, azithromycin, claforan, clarithromycin, dirithromycin, erythromycin, lincomycin, troleandomycin, bacampicillin, carbenicillin, cloxacillin, dicloxacillin, meticillin, mezlocillin, nafcillin, oxacillin, piperacillin, ticarcillin, cinoxacin, ciprofloxacin, enoxacin, grepafloxacin, levofloxacin, lomefloxacin, nalidixic acid, norfloxacin, ofloxacin, sparfloxacin, sulfisoxazole, sulfacytine, sulfadiazine, sulfamethoxazole, sulfisoxazole, dapson, aztreonam, bacitracin, capreomycin, chloramphenicol, clofazimine, colistimethate, colistin, cycloserine, fosfomycin, furazolidone, methenaminc, nitrofurantoin, pentamidine, rifabutin, rifampin, spectinomycin, tigecycline, trimethoprim, trimetrexate glucuronate, vancomycin, chlorhexidine and carbapenem antibiotics such as ertapenem. According to some embodiments the antibiotic agent is an antibiotic peptide. Each antibiotic represents a separate embodiment of the present invention.

According to some currently preferred embodiments, the antibiotic agent of methods and compositions of the present invention is a tetracycline. In one embodiment, the tetracycline is doxycycline. In another embodiment, the antibiotic is a hydrophobic tetracycline. Non-limiting examples of hydrophobic tetracyclines are 6-demethyl-6-deoxytetracycline, 6-methylene tetracycline, minocycline (also known as 7-dimethylamino-6-demethyl-6-deoxytetracycline), and 13-phenylmercapto-a-6-deoxy-tetracycline. In another embodiment, the antibiotic is selected from the group consisting of doxycycline, tetracycline, and minocycline.

In another embodiment, the antibiotic is doxycycline or doxycycline hyclate. Doxycycline can be effectively used for treating surgical site infections caused by many types of both Gram-negative and Gram-positive bacteria and is used for treating a number of conditions. Most importantly, Doxycycline is highly effective against *Staphylococcus aureus* (*S. aureus*), the most common bacteria causing surgical site infections. Furthermore, bacteriologic testing indicates appropriate susceptibility to doxycycline by Methicillin-resistant *Staphylococcus aureus* (MRSA). The minimal inhibitory concentrations (MIC) of Doxycycline against common bacteria, as well as such *S. aureus* are relatively low, and can be as low as 0.1 µg/ml (for *S. aureus*), allowing high potency in vivo against surgical site infections.

According to some embodiments, the pharmaceutically active agent used in methods according to some embodiments of the invention is an antifungal agent selected from the group consisting of amphotericin B cholesteryl sulfate complex, natamycin, amphotericine, clotrimazole, nystatin, amphotericin B lipid complex, fluconazole, flucytosine, griseofulvin, itraconazole, ketoconazole, benzoic acid and salicylic acid, betamethasone and clotrimazole, butenafine, carbol-fuchsin, ciclopirox, clioquinol, clioquinol and hydrocortisone, clotrimazole, econazole, gentian violet, haloprogin, iodoquinol and hydrocortisone, ketoconazole, miconazole, naftifine, nystatin, nystatin and triamcinolone, oxiconazole, sodium thiosulfate, sulconazole, terbinafine, tolnaftate, triacetin, undecylenic acid and derivatives thereof, butoconazole, clotrimazole, sulfanilamide, terconazole, and tioconazole.

According to some embodiments, the matrix composition of the invention may comprise, in addition to the antibiotic agent and/or antifungal agent, another pharmaceutically active agent selected from steroids and/or non-steroidal anti-inflammatory drugs (NSAID).

Any suitable NSAID may be integrated into the matrix composition for sustained and/or controlled release. Non limiting examples of NSAID include ibuprofen, flurbiprofen, aminosalicylate sodium, choline magnesium trisalicylate, choline salicylate, diclofenac, diflunisal, etodolac, fenoprofen, indomethacin, ketoprofen, ketolac tromethamine, magnesium salicylate, meclofenamate, mefenamic acid, nabumetone, naproxen, oxaprozin, oxyphenbutazone, piroxicam, salsalate, sulindac and tolmetin. Each NSAID listed represents a separate embodiment of the present invention.

Any suitable steroidal anti-inflammatory drug may be integrated into the matrix composition. Non limiting examples of steroidal anti-inflammatory drugs (SAIDs) to be used in the formulations of the present invention include, but are not limited to, Corticosteroids such as: betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide, cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol.

In specific embodiments, the matrix composition is substantially free of water. "Substantially free of water" as used herein refers, in one embodiment, to a composition containing less than 5% water by weight. In another embodiment, the term refers to a composition containing less than 4.5% water by weight. In another embodiment, the term refers to a composition containing less than 4.0% water by weight. In another embodiment, the term refers to a composition containing less than 3.5% water by weight. In another embodiment, the term refers to a composition containing less than 3.0% water by weight. In another embodiment, the term refers to a composition containing less than 2.5% water by weight. In another embodiment, the term refers to a composition containing less than 2.0% water by weight. In another embodiment, the term refers to a composition containing less than 1.5% water by weight. In another embodiment, the term refers to a composition containing less than 1.0% water by weight. In another embodiment, the term refers to the absence of amounts of water that affect the water-resistant properties of the composition. In another embodiment, the term refers to a composition manufactured without the use of any aqueous solvents. In another embodiment, producing the composition using a process substantially free of water, as described herein, enables lipid saturation. Lipid saturation confers upon the matrix composition ability to resist bulk degradation in vivo; thus, the matrix composition exhibits the ability to mediate extended release on a scale of several days, weeks or months.

In another embodiment, the matrix composition is substantially free of unbound water. In another embodiment, the term refers to a composition not containing detectable amounts of unbound water. The term "unbound water"—refers to free water, which is not part of the thin water film (usually a few molecules thick) formed on the surface of macromolecules (e.g. phospholipids and polymers). The total amount of water in the composition may be determined by any method known in the art such as Karl Fischer and loss on drying methods. The ratio between bound and unbound water may be determined for example by differential scanning calorimeter (DSC).

Technology Platform of the Substrate Impregnated or Coated Fully or Partially with the Matrix Composition Used in Methods of the Present Invention According to some embodiments, the coating matrix composition has a highly organized multilayer structure in which the polymer and associated cholesterol form one type of layer, the phospholipids form a second type of layer, and the two types of layers are organized in the form of multiple alternating or quasi-alternating layers.

According to some embodiments, the coating matrix composition of the present invention comprises a continuous structure devoid of internal gaps and/or free volume. According to some embodiments, the coating matrix composition is lipid-saturated, indicating that the space between the polymer layers or polymer backbone is filled with lipid molecules in combination the pharmaceutically active agent (e.g. an antibiotic agent and/or antifungal agent), to the extent that additional lipid moieties can no longer be incorporated into the matrix to an appreciable extent.

The coating matrix compositions disclosed herein are lipid saturated. "Lipid saturated," as used herein, refers to saturation of the polymer of the matrix composition with the first lipid component (e.g. cholesterol) and the second lipid component (e.g. phospholipids) in combination with any pharmaceutical agent present in the matrix, and any other lipids that may be present. The matrix composition is saturated by whatever lipids are present. In another embodiment, "lipid saturation" refers to filling of internal gaps (free volume) within the lipid matrix as defined by the external border of the polymeric backbone. The gaps are filled with phosphatidylcholines in combination with cholesterol and possibly other type of lipids and antibiotic agent present in the matrix, to the extent that additional lipid moieties can no longer be incorporated into the matrix to an appreciable extent. Lipid-saturated matrices of the present invention exhibit the additional advantage of not requiring a synthetic emulsifier or surfactant such as polyvinyl alcohol; thus, matrix compositions of the present invention are typically substantially free of polyvinyl alcohol.

In some embodiments, the coating matrix composition is capable of releasing at least 30% of the active agent at zero-order kinetics when it is maintained in an aqueous medium (when it is hydrated). In some embodiments, at least 40% of the pharmaceutically active agent is released from the matrix composition at zero-order kinetics when it is maintained in an aqueous medium. In some embodiments, at least 50% of the pharmaceutically active agent is released from the matrix composition at zero-order kinetics when it is maintained in an aqueous medium. Without being limited by a specific theory or mechanism of action it is suggested that the organized structure or substructure of the matrix composition of the invention is one of the main reasons for the zero-order release rate of the drug or drugs from the matrix formulation following its hydration. Thus, the zero order release rate may be attributed to slow and continuous "peeling" of the hydrated surface layer(s) of the highly organized layers of lipids and polymer, with concomitant release of the drug as the components of the surface layer are removed from the matrix. It is surmised that this process slowly repeats itself, releasing drug(s) at a steady rate over days, weeks or even months, until the matrix has been completely degraded. Without wishing to be bound by theory, it is believed that the polymer form a first type of layer, and that the phospholipid(s) forms a second type of layer, and that these layers alternate i.e. (polymer)-(phospholipid)-(polymer)-(phospholipid); the term "quasi-alternation" is used herein to refer to the situation in which there is alternation of more than one instance of a type of layer, e.g. (polymer)-(phospholipid)-(phospholipid)-(polymer)-(phospholipid)-(phospholipid)-(polymer). It is assumed that the cholesterol molecules are located in between the two layer, the polar head group pointing towards the polymer and the hydrophobic part between the phospholipid molecules.

In some embodiments, the matrix composition has multiple mixed layers of polymer and phospholipid as described supra and it is not in the form of a microsphere, a micelle, a reversed micelle or a liposome. In some embodiments, the matrix composition does not comprise micelles, reverse micelles or liposomes.

According to some embodiments the matrix of the present invention is water resistant. As such water cannot easily, if at all, diffuse into the inner layers of the matrix and the pharmaceutically active agent entrapped between the inner layers cannot easily, if at all, diffuse out of the matrix. More particularly it refers to a composition having its hulk (e.g. part of the composition which is surrounded by an external surface, said external surface is exposed to the surrounding environment) not exposed to water, or exposed to the extent that the amount of penetrating water is small and insufficient to cause matrix bulk disintegration or degradation. Without wishing to be bound by theory or mechanism of action, the water resistance properties of the matrix composition, together with its unique multilayered structure confer the matrix with its sustained release properties, e.g. its ability to release at least 30% of the pharmaceutically active agent (e.g. an antibiotic agent) from the composition at zero order kinetics for periods of time ranging from several days, weeks and even months, when the composition is maintained in an aqueous environment at physiological temperature.

The efficacy of a drug is commonly determined by its local concentration. That, in turn, is determined by the ratio between the accumulation rate of drug released from the product vs. its elimination by physical distribution to surrounding tissue, as well as by neutralization and/or degradation. An optimal drug delivery system should release the drug according to the biological need, in order to create an effective concentration at close proximity to the target and throughout a sufficient period of time needed for the desired biological effect. This can be achieved by releasing the active form of the drug near the target at a rate that will result in an effective concentration that is above the minimal effective rate, but below the toxic level and for the desired period of time needed for effective therapeutic effect.

One of the ways to gain better control over local exposure of a given drug is by controlling its supply rate. The supply rate is dictated by 1) the drug release profile, 2) the release rate and 3) the duration of release. These parameters are closely related; while the release rate is strongly depended on the specific formulation, the duration is a function of two factors: release rate and the size of drug reservoir.

The matrix composition of the invention comprising a combination of specific lipids and polymers loaded with a drug, preferably an antibiotic agent, determines not only the release rate profile of the drug, but also allows control over the release rate during a prolonged zero-order kinetic stage. Without wishing to be bound by theory or mechanism of action it is suggested that the most effective profile will combine initial release, resulting with an effective local concentration of the drug, followed by continuous, zero order kinetics, release over sufficient duration, for example up to 2 months, up to 7 weeks, up to 6 weeks, up to 5 weeks, up to 4 weeks, up to 3 weeks, up to 2 weeks, preferably at least 3-4 weeks. The initial release should be limited so as to leave sufficient reservoir to support subsequent prolong release.

According to some embodiments, when maintained in an aqueous medium at physiological temperatures, 1 to 50% of said pharmaceutically active agent is released from the matrix composition by the end of the first day, 10 to 100% of said pharmaceutically active agent is released from the matrix composition by the end of the first week, 20 to 100% of said pharmaceutically active agent is released from the matrix composition by the end of the first two weeks and 30 to 100% of said pharmaceutically active agent is released by the end of the first three weeks. In some embodiments, when maintained in an aqueous medium at physiological temperatures, at least 10% but not more than 60% of the pharmaceutically active agent is released by the end of the first week, at least 20%, but not more than 80% of the pharmaceutically active agent is released by the end of the second week, at least 30% of the pharmaceutically active agent is released by the end of the third week. At least 40% of the pharmaceutically active agent is released by the end of the third week. At least 50% of the pharmaceutically active agent is released by the end of the third week. At least 60% of the pharmaceutically active agent is released by the end of the third week. According to currently preferred embodiments, the pharmaceutically active agent is an antibiotic agent.

According to some exemplary embodiments, It has been shown (see Examples 1 and 2) that substrate particles (e.g. tri-calcium phosphate or polyvinyl alcohol) impregnated/coated with a matrix composition comprising about 15-25% (w/w) of PLGA, about 5-15% (w/w) of cholesterol, about 50-70% (w/w) of a mixture of DPPC and DSPC wherein the ratio of DPPC and DSPC is between about 5:1 and 2:1 and about 7-12% (w/w) of doxycycline, displays initial release of up to about 35% of the entrapped antibiotic and preferably up to 30% of the entrapped antibiotic. The amount of drug released immediately post hydration is clinically safe and leaves most of the drug (at least 65%) to prolonged delivery for at least 30 days. and can elevate local concentration of doxycycline to 10-50 MIC or more. The substrate impregnated or coated fully or partially with the matrix composition used in methods of the present invention gradually releases the pharmaceutically active agent (e.g. antibiotic agent) at a constant release rate (between about 1.5-5% (weight percent of the pharmaceutically agent released per day/total weight of pharmaceutically active agent initially encapsulated in the matrix composition)), resulting with a local concentration of the drug that is at least 10 times the (minimal inhibitory concentration (MIC) of the antibiotic against pathogens most common is cases of surgical site infection (e.g. *S. aureus* bacteria) over up to 5 weeks.

The substrate impregnated or coated fully or partially with the matrix composition used in methods of the present invention enables to entrap a large variety of one or more biologically active molecules and to release them at a pre-programmed rate for periods ranging from several days to several weeks.

The substrate impregnated or coated fully or partially with the matrix composition used in methods of the present invention releases the pharmaceutically active agent locally at a predictable, long-term rate. Thus, the therapeutic drug levels can be maintained locally at the surgical site (e.g. incision site), while maintaining low or no systemic levels. Due to the prolonged local release of the pharmaceutical agent, a small and safe dose of local pharmaceutical agent, which, in some cases, be equal to not more than a single dose commonly administered IV, is highly effective in eradicating local bacterial infections in surgical sites. By way of example, the amount of antibiotic (e.g. doxycycline) in 5 grams of the substrate impregnated or coated fully or partially with the matrix composition used in methods of the present invention is about the same as the amount of antibiotic in a single dose commonly administered I.V. or a single pill (or tablet) for oral use.

Additionally, the coating matrix composition acts like a reservoir in which the entrapped pharmaceutical agent is protected. In contrast to the conventional polymer based delivery systems, this characteristic can protect sensitive drugs reservoir not only from biological degradation agents such as enzymes, but also from chemical destruction due to in vivo soluble materials and hydration. When prolong effect is needed, this characteristic is becoming highly important.

"Zero-order release rate" or "zero order release kinetics" means a constant, linear, continuous, sustained and controlled release rate of the pharmaceutical active agent from the polymer matrix, i.e. the plot of amounts of pharmaceutical active agent released vs. time is linear. According to some embodiments, at least 30% of the pharmaceutically active agent is released from the matrix composition at zero order kinetics at a rate between about 1-7%, 1.5-6%, 1.5-5%, 2-4%, 1.5-3% (weight percent of the pharmaceutically agent released per day/total weight of pharmaceutically active agent initially encapsulated in the composition), each possibility represent a separate embodiment of the invention.

Lipids

"Phospholipids" are phosphoglycerides having a single phosphatidyl linkage on a glycerol backbone and fatty acids at the remaining two positions. However, it is to be understood explicitly that phosphoglycerides having hydrocarbon chains other than fatty acid residues including alkyl chains, alkenyl chains or any other hydrocarbon chain of at least 12 carbons, alternatively, at least 14 carbons are included within the scope of the present invention. The linkage may be an ether linkage instead of an acyl linkage found in phospholipids.

"Phosphatidylcholine" refers to a phosphoglyceride having a phosphorylcholine head group. This phospholipid is composed of a choline head group and glycerophosphoric acid, with a variety of fatty acids moieties. The fatty acids moieties are typically naturally occurring. In some embodiments, the fatty acid moieties are saturated. In some embodiments, the fatty acid moieties are unsaturated. "Saturated", refers to the absence of a double bond in the hydrocarbon chain. In another embodiment, the fatty acid moieties have at least 12 carbon atoms. In another embodiment, the fatty acid moieties have 14 carbon atoms. In another embodiment, the fatty acid moieties have 16 carbon atoms. In another embodiment, the fatty acid moieties have 18 carbon atoms. In another embodiment, the fatty acid moieties have 14-18 carbon atoms. In another embodiment, the fatty acid moieties have 14-16 carbon atoms. In another embodiment, the fatty acid moieties have 16-18 carbon atoms. In another embodiment, the fatty acid moieties are chosen such that the gel-to-liquid-crystal transition temperature of the resulting matrix is at least 40° C. In another embodiment, the fatty acid moieties are both arachidoyl. Each possibility represents a separate embodiment of the present invention.

In another embodiment, the phosphatidylcholine is a naturally-occurring or a synthetic phosphatidylcholine. According to one embodiment, the phosphatidylcholine is a symmetric phosphatidylcholine (i.e. a phosphatidylcholine wherein the two fatty acid moieties are identical (e.g.) dimyristoyl phosphatidylcholine (DMPC), dipalmitoyl-phosphatidylcholine (DPPC), 1,2-distearoyl-sn-glycero-3-phosphocholine (DSPC), dioleoyl-phosphatidylcholine (DOPC). In another embodiment, the phosphatidylcholine is an asymmetric phosphatidylcholine (e.g. 1-palmitoyl-2-stearoylphosphatidylcholine (PSPC); 1-palmitoyl-2-oleoyl-phosphatidylcholine (POPC), 1-Stearoyl-2-Arachidonoyl-Phosphatidylcholine (SAPC), 2-Arachidonoyl-1-palmitoyl-sn-glycero-3-phosphocholine (APPC)). In another embodiment, the phosphatidylcholine is any other phosphatidylcholine known in the art. Each phosphatidylcholine represents a separate embodiment of the present invention.

According to certain embodiments, the at least one phosphatidylcholine in matrix composition suitable for preventing and/or treating surgical site infections is selected from the group consisting of DMPC, DPPC, DSPC, DOPC and any combination thereof. Alternatively, the at least one phosphatidylcholine is selected from DMPC, DPPC or a combination thereof. Alternatively, the at least one phosphatidylcholine is selected from DPPC, DSPC or a combination thereof. Alternatively, the at least one phosphatidylcholine is selected from DMPC, DPPC or a combination thereof. Alternatively, the at least one phosphatidylcholine is selected from DMPC, DOPC or a combination thereof.

"Phosphatidylethanolamine" consists of a combination of glycerol esterified with two fatty acids and phosphoric acid. Whereas the phosphate group is combined with ethanolamine. In one embodiments, the fatty acids moieties may be saturated or unsaturated. In another embodiment, the fatty acid moieties have at least 14 carbon atoms. In another embodiment, the fatty acid moieties have at least 16 carbon atoms. In another embodiment, the fatty acid moieties have 14 carbon atoms. In another embodiment, the fatty acid moieties have 16 carbon atoms. In another embodiment, the fatty acid moieties have 18 carbon atoms. In another embodiment, the fatty acid moieties have 14-18 carbon atoms. In another embodiment, the fatty acid moieties have 14-16 carbon atoms. In another embodiment, the fatty acid moieties have 16-18 carbon atoms. In another embodiment, the fatty acid moieties are chosen such that the gel-to-liquid-crystal transition temperature of the resulting matrix is at least 40° C. The two fatty acids may be the same, or different, and are usually attached to the 1,2 positions of the glycerol moiety. Non limiting examples of suitable phosphatidylethanolamines are dimethyl dimyristoyl phosphatidylethanolamine (DMPE), dipalmitoyl-phosphatidylethanolamine (DPPE), dilauroylphosphatidylethanolamine (DLPE), distearoylphosphatidylethanolamine (DSPE), dioleoylphosphatidylethanolamine (DOPE), 1-palmitoyl-2-oleylphosphatidylethanolamine (POPE), 1-oley 1-2-palmitoylphosphatidylethanolamine (OPPE), and dierucoylphosphatidylethanolamine (DEPE). In another embodiment, the phosphatidylethanolamine is any other phosphatidylethanolamine known in the art. Each phosphatidylethanolamine represents a separate embodiment of the present invention.

"Sterol" in one embodiment refers to a steroid with a hydroxyl group at the 3-position of the A-ring. According to some embodiments, the sterol constitutes up to about 40% (w/w) of the weight of the matrix composition. In another embodiment, the sterol of methods and compositions of the present invention is a zoosterol. In another embodiment, the sterol is cholesterol.

In another embodiment, a composition of the present invention further comprises a lipid other than phosphatidylcholine, phosphatidylethanolamine, or a sterol. In another embodiment, the additional lipid is a phosphoglyceride. In another embodiment, the additional lipid is selected from the group consisting of a phosphatidylserine, a phosphatidylglycerol, and a phosphatidylinositol. In another embodiment, the additional lipid is selected from the group consisting of a phosphatidylserine, a phosphatidylglycerol, a phosphatidylinositol, and a sphingomyelin. In another embodiment, the additional lipid is selected from the group consisting of a phosphatidylserine, a phosphatidylglycerol, a phosphatidylinositol, a sphingomyelin and a ceramide. In another embodiment, a combination of any 2 or more of the above additional lipids is present. In another embodiment, the polymer, phosphatidylcholine, phosphatidylethanolamine, sterol, and additional lipid(s) are all incorporated into the matrix composition. Each possibility represents a separate embodiment of the present invention.

Additional Components

In another embodiment, a matrix composition of methods and compositions of the present invention further comprises a free fatty acid. Non limiting examples of free fatty acids that can be incorporated in the coating matrix composition of the invention are selected from omega-6 fatty acid, omega-9 fatty acid, a free fatty acid having 14 or more carbon atoms, a free fatty acid having 16 or more carbon atoms, a free fatty acid having 16 carbon atoms, a free fatty acid having 18 carbon atoms, a free fatty acid having 16-22 carbon atoms, a free fatty acid having 16-20 carbon atoms, a free fatty acid having 16-18 carbon atoms, a free fatty acid having 18-22 carbon atoms, a free fatty acid having 18-20 carbon atoms, linoleic acid, linolenic acid and oleic acid. In another embodiment, the free fatty acid is another appropriate free fatty acid known in the art. In another embodiment, the free fatty acid adds flexibility to the matrix composition. In another embodiment, the free fatty acid slows the in vivo release rate. In another embodiment, the free fatty acid improves the consistency of the in vivo controlled release. The fatty acid may be unsaturated or saturated. In another embodiment, incorporation of a saturated fatty acid having at least 14 carbon atoms increases the gel-fluid transition temperature of the resulting matrix composition. Each type of fatty acid represents a separate embodiment of the present invention.

In another embodiment, a matrix composition of methods and compositions of the present invention further comprises a tocopherol (e.g. E307 (α-tocopherol), β-tocopherol, E308 (γ-tocopherol), E309 (δ-tocopherol). According to some embodiments, the tocopherol may be incorporated into the matrix instead or in addition to the first lipid having a polar group (e.g. a sterol, a cholesterol). Each possibility represents a separate embodiment of the present invention.

In another embodiment, a matrix composition of methods and compositions of the present invention further comprises physiologically acceptable buffer salts, which are well known in the art. Non-limiting examples of physiologically acceptable buffer salts are phosphate buffers. A typical example of a phosphate buffer is 40 parts NaCl, 1 part KCl, 7 parts $Na_2HPO_4$ $2H_2O$ and 1 part $KH_2PO_4$. In another embodiment, the buffer salt is any other physiologically acceptable buffer salt known in the art. Each possibility represents a separate embodiment of the present invention.

Therapeutic Methods

The methods of the invention directed at preventing and treating surgical site infections address medical needs that are currently lacking effective solutions and that are of great concern to the medical community. The methods of the present invention provide localized infection treatment and prevention to be applied during and/or after surgical procedures. The methods of the invention reduce the overall infection rate and overcome or reduce existing infections, including hospital-acquired resistant bacteria. The methods of the invention may be used for treatment and prophylaxis of postoperative infections in a variety of tissues and solid organs.

According to some embodiments the methods for preventing, inhibiting or treating a surgical site infection in a subject are suitable for suppressing surgical site infections in general and in particular, surgical site infections associated with orthopedic surgical operations (e.g. hip arthroplasty, knee arthroplasty, total joint replacement, trauma), spine surgical operations, surgical operations on a digestive system organ (e.g. esophagus, stomach, small intestine, large intestine, rectum, colon, appendix, liver, pancreas, gallbladder, gastric ulcer, gastric cancer procedures, open gastric bypass, appendectomy, colectomy, cholecystectomy, vagotomy, open binary tract procedures, small intestine procedures, colorectal procedures), cardiac procedures (e.g. coronary artery bypass, cardiothoracic transplantation procedures, cardiac device insertion procedures), hernia repair, vascular procedures, caesarian, prostatectomy, obstetric and gynecologic surgical operations (e.g. hysterectomy), head and neck cancer surgery, transplantation surgeries (e.g. lung, liver, pancreas, kidney), neurosurgery (e.g. deep brain stimulation implant) and plastic surgeries (e.g. breast reconstruction, mastectomy).

According to specific embodiments, the present invention provides methods for preventing, inhibiting or treating sternal wound site infection associated with cardiac surgery procedures comprising the step of applying to the sternal halves surface and/or surrounding soft tissue a biodegradable substrate being impregnated and/or having its surface coated fully or partially with a matrix composition comprising (a) a biocompatible polymer, (b) a first lipid component comprising a sterol, (c) a second lipid component comprising at least one phospholipid having fatty acid moieties of at least 12 carbons; and (d) a pharmaceutically active agent selected from the group consisting of an antibiotic agent, antiseptic agent, an anti-inflammatory agent, anti-fungal agent and any combination thereof. According to some embodiments, the pharmaceutically active agent is an antibiotic agent. According to some embodiments, the antibiotic agent is doxycycline or doxycycline hyclate. The methods for preventing, inhibiting or treating sternal wound infection associated with cardiac surgery further encompass the prevention or suppression of sternal wound biofilm formation following cardiac surgery. As used herein, "sternal wound site infection" encompasses both superficial and deep sternal wound complications.

According to specific embodiments, the present invention provides methods for preventing, inhibiting or treating sternal wound site infection associated with cardiac surgery procedures comprising the step of applying to the sternal halves surface and/or surrounding soft tissue, tri-calcium phosphate particles or polyvinyl alcohol particles impregnated/coated with a matrix composition comprising about 15-25% (w/w) of PLGA, about 5-15% (w/w) of cholesterol, about 50-70% (w/w) of a mixture of DPPC and DSPC wherein the ratio of DPPC and DSPC is between about 5:1 and 2:1 and about 7-12% (w/w) of doxycycline.

According to some embodiments, the substrate impregnated or coated fully or partially with the composition according to the methods of the invention, may be administered to the surgical site (e.g. incision site) directly to or proximal to the site of incision. In some embodiments, the impregnated/coated substrate may be administered to the surgical site (e.g. incision site) by sprinkling the impregnated/coated substrate particles onto a surgical site and its vicinity. According to some embodiments the coated substrate is formulated as a powder. According to some embodiments, coated substrate particles may be sprinkled over the surgical site and its vicinity using a salt shaker-like container or dispenser. A salt shaker-like container or dispenser as used herein refers to a container defining a cavity (e.g. a tubular cavity) for storing the coated substrate powder, and which has at least one aperture through which the coated substrate particles may be dispensed. In another embodiment, the substrate impregnated or coated fully or partially with the composition according to some embodiments of the invention, may be injected to the surgical site (e.g. incision site) and its surroundings. Alternatively, substrates in the form of a sponge, a foam or a sheet impregnated or coated fully or partially with the composition according to some embodiments of the invention, may be administered to the surgical site by placing them over the surgical site or its surrounding, for example by covering the surgical site with at least one piece of a gelatin or collagen sponge, foam or sheet impregnated or coated with the matrix composition. Alternatively, the biocompatible substrates impregnated or coated fully or partially with the composition according to some embodiments of the invention, may be formulated as a paste and spread over the surgical site and its vicinity. Typically, a paste like structure is obtained by hydrating a drug coated substrate disclosed herein with an aqueous solution prior to its application. According to some embodiments, hydration shall be performed not more than 2 hours prior to the application of the resulting paste to the surgical site, preferably up to 1 hour prior to the application of the resulting paste to the surgical site, more preferably, not more than 30 minutes prior to its application to the surgical site. According to some embodiments, a paste texture will be attained when the amount of aqueous solution (for example: saline) mixed with the drug coated substrates is between 0.1:1 and 1:1 (w/w) respectively; preferably between 0.3:1 and 0.6:1 (w/w) respectively.

The present invention provides methods for preventing or treating a surgical site infection associated with a surgical operation comprising the step of applying to the surgical site a biodegradable substrate being impregnated and/or having its surface coated fully or partially with a matrix composition which provides local controlled and prolonged release of at least one pharmaceutically active agent at the surgical site. In some embodiment the matrix composition incorporates a plurality of pharmaceutically active agents. According to some embodiments, the substrate coated with the matrix composition of the present invention may be administered substantially as a single ingredient (not administered as part of a mixture with other ingredients). Alternatively, it may be applied to the surgical site as a combination of two or more populations of differently coated substrates. For example, the methods may comprise the step of applying to the surgical site a combination of a first population of coated substrates comprising one antibiotic agent mixed with a second population of coated substrates comprising a different antibiotic agent.

As described above, the amounts, ratios and types of ingredients forming the matrix composition of the present invention may be varied so to adjust the polymer-lipid basis to the biophysical/biochemical properties of the drug, the therapeutically effective dose of the drug and to the desired release rate and/or the duration of release of the drug. The methods of the invention therefore encompass the step of application to the surgical site of a combination of two or more populations of coated substrates, each capable of releasing the drug at a different rate and/or duration, the drug in the different coated substrate populations may be the same or different. Without wishing to be bound by theory or mechanism of action, application to the surgical site of a combination of coated substrate populations, each comprising a different drug formulated to be released at a predetermined rate and/or duration, provides the clinician or skilled artisan with great flexibility in adjusting the treatment protocol according to the medical need. A non-limiting example may be a combination of two populations of drug coated substrates, one comprising a first antibiotic agent released for about 3-4 weeks and a second population of drug coated substrates comprising a second antibiotic agent released for about 1-2 weeks.

It is to be emphasized that the substrates coated/impregnated with a matrix composition according to embodiments of the invention, may be provided to the clinician or skilled artisan as a pre-mixed combination of two or more populations of coated substrate or preferably, as single ingredients (not part of a mixture with other ingredients) to be mixed by the skilled artisan prior to application to the surgical site.

Methods of Making Matrix Compositions

In order to obtain the compositions of the invention any suitable method may be employed that will yield a homogeneous dispersion of the polymer and the lipids in a water resistant matrix. Advantageously according to some embodiments the methods employed eschew the use of water at any stage of the manufacturing process.

Advantageously, the matrix compositions of the present invention are prepared by methods which do not involve the formation of emulsions, and may avoid the use of aqueous media altogether. The generation of emulsions that are subsequently dried necessarily results in vesicles or microspheres. In order to produce coated articles the mixture of polymer, lipids and antibiotics within the appropriate selected volatile organic solvents will be used to coat the desired surface.

According to some embodiments the polymer and sterol are mixed with appropriate selected volatile organic solvent(s) on the one hand and the phospholipids together with the active pharmaceutical agent are mixed with its appropriate selected solvent(s) or solvents prior to mixing together with the polymer/sterol mixture.

In certain embodiments, the present invention provides a method of producing a matrix composition, the method comprising the steps of:

(a) mixing into a first volatile organic solvent: (i) a biodegradable polyester and (ii) sterol; and (b) mixing separately into a second volatile organic solvent: (i) an active agent; (ii) a phosphatidylcholine or a mixture of phosphatidylcholines and optionally (iii) an additional lipid component such as, for example, a phosphatidylethanolamine;

(c) mixing and homogenizing the products resulting from steps (a) and (b); and (d) bringing the substrate into contact with the homogenous mixture resulting from step (c).

In another embodiment, phosphatidylethanolamine may be included in the volatile organic solvent of step (a) instead of or in addition to a phosphatidylethanolamine added to the volatile organic solvent of step (b). In another embodiment, the biodegradable polyester is selected from the group consisting of PLA, PGA and PLGA. In another embodiment, the biodegradable polyester is any other suitable biodegradable polyester known in the art. In some embodiments the first volatile organic solvent is a non-polar solvent. In some embodiments the second volatile organic solvent is a water miscible solvent. In cases where the active agent is a protein or peptide it is important to select solvents that will not denature or impair the activity of the protein.

In another embodiment, the mixture of step (a) containing a volatile organic solvent is homogenized prior to mixing it with the solution of step (b). In another embodiment, the volatile organic solvent or mixture of volatile organic solvents used in step (a) may be same or different than the volatile organic solvent or mixture of organic solvents used in step (b). In another embodiment, the mixture of step (b) is homogenized prior to mixing it with the mixture of step (a). In another embodiment, the polymer in the mixture of step (a) is lipid saturated. In another embodiment, the matrix composition is lipid saturated. Preferably, the polymer and the phosphatidylcholine are incorporated into the matrix composition. In another embodiment, the active agent as well is incorporated into the matrix composition.

In another embodiment, each step of the production method is substantially free of aqueous solution. In another embodiment, each step is substantially free of the presence of water or any aqueous solution.

Upon mixing, a homogenous mixture is formed. The substrate to be coated or impregnated with the matrix composition is combined with said homogenous mixture.

The production method further comprises the step of evaporating the solvent present in the product of step (d). Solvent evaporation is typically done by heating the product of step (d). The heating is continuing until the solvent is eliminated and in a typical temperature between room temperature to 60° C., preferably at a temperature below 50° C., more preferably at a temperature of 45° C. or lower, more preferably at a temperature of 30° C. or lower. According to some embodiments, mild vacuum (e.g. 300-600 psi) is applied during the solvent evaporation step. In another embodiment a step of vacuum-drying is performed following the step of solvent evaporation. Each possibility represents a separate embodiment of the present invention.

Methods for the determination of lipid saturation: The following method may be used to determine the degree of lipid saturation:

(i) Following manufacture, the matrix composition is hydrated and isolated by centrifugation or filtration. Lipids that not entrapped in the matrix form free micelles or liposomes and are located in the supernatant. The overall lipid contents of the supernatant and the matrix are quantified. In this manner, the entrapped vs. free lipid contents are determined for various formulation containing different lipid:polymer ratios at the outset. Thus, the actual, experimental, maximum lipid/polymer ratio is determined.

(ii) Following manufacture, the matrix composition is hydrated with a solution containing tritium-tagged water, washed with tritium-free solution, and isolated by centrifugation or filtration, and the amount of water entrapped per polymer mass is quantified. This is repeated with different lipid:polymer ratios, in order to determine the amount of lipids required to saturate the free volume in the matrix composition.

EXPERIMENTAL DETAILS SECTION

Abbreviations used: phosphoethanolamine=PE; phosphatidylcholine=PC; 1,2-dimyristoyl-sn-glycero-3-phosphoethanolamine=DMPE (14:0); 1,2-dipalmitoyl-sn-glycero-3-phosphoethanolamine=DPPE (16:0); 1,2-distearoyl-sn-glycero-3-phosphocholine=DS PC (18:0); 1,2- dipalmitoyl-sn-glycero-3-phosphocholine=DPPC (16:0); Tri-calcium phosphate (TCP); poly vinyl alcohol (PVA).

Example 1: Process for the Preparation of a Substrate (e.g. Tri-Calcium Phosphate Particles, Poly Vinyl Alcohol Particles) Coated/Impregnated with a Doxycycline Containing Matrix Composition According to Certain Embodiments of the Invention (for the Treatment and Prevention of Surgical Site Infections)

Overview: To produce lipid-saturated polymer matrices, two mixtures are created.

1. A biodegradable polymer and a first lipid component (e.g. sterol) are mixed with a volatile organic solvent, which is mixed to yield a solution or suspension of lipid-saturated polymer matrix, as measured by its differential scanning calorimetric (DSC) profile.
2. The active agent and a second lipid component (e.g. at least one phospholipid) are mixed with a second volatile organic solvent to yield a second solution or suspension.
3. The two solutions or suspensions are combined and mixed until equilibrium is reached.
4. A substrate (e.g. gelatin sponge, collagen foam, mineral substrate) is then mixed with the resulting solution of stage 3.
5. The organic solvents are then evaporated, yielding a substrate coated and/or impregnated with a drug-containing, lipid-saturated polymer matrix.

Exemplary Protocol

Tri-calcium phosphate particles having an average diameter of 100 μm were coated with a matrix composition suitable for sustained release of doxycycline by the following process:

1. Preparation of Stock Solutions:
  1.1. Stock solution of PLGA 75/25 (300 mg/ml in ethyl acetate)—PLGA 75/25 was weighed into volumetric flask. Ethyl acetate was added to volume. The solution was stirred until all PLGA grains were completely dissolved.
  1.2. Stock solution of Cholesterol (30 mg/ml in ethyl acetate)—Cholesterol was weighed into volumetric flask. Ethyl acetate was added to volume. The solution was vortexed until the cholesterol was completely dissolved.
  1.3. Stock solution of Doxycycline (210 mg/ml in methanol)—Doxycycline was weighed into volumetric flask. Methanol was added to volume. The solution was vortexed until the doxycycline was completely dissolved.
  1.4. Stock solution of DPPC (206 mg/ml and DSPC 69 mg/ml in methanol/ethyl acetate mixture (9/14))—DPPC and DSPC were weighed into volumetric flask. Methanol/ethyl acetate (9/14) was added to volume. The solution was incubated at 45° C. for 5 min and vortexed until the phospholipids were completely dissolved.
2. Preparation of the Coating Solution
  Solution A—5 volumes of the cholesterol stock solution were mixed with 1 volume of the PLGA stock solution. The mixture contained 50 mg/ml PLGA and 25 mg/ml cholesterol. Solution B—18 volumes of doxycycline solution were successfully mixed with 82 volumes of phospholipids solution (see section 1.4). The mixture contained 225 mg/ml phospholipids (56 mg/ml DSPC and 169 mg/ml DPPC) and 37.5 mg/ml doxycycline. Solution AB—2 volume of solution B were mixed with 3 volumes of solution A resulting solution containing 30 mg/ml PLGA 75/25, 15 mg/ml cholesterol, 90 mg/ml phospholipids and 15 mg/ml doxycycline.
3. Substrate Coating
  1.5 gr. of substrate (e.g. tri-calcium phosphate powder (100 μm particles), poly vinyl alcohol (PVA) powder, Poly lactic acid (PLA) powder) were weighed into 30 mm glass petri dish.
  1.5 ml of solution AB was added to the dish.
  The petri dish was placed in a vacuum oven set to 45° C. and partial vacuum was applied ((~610 mm/Hg) until all solvents evaporated (the presence of solvents could not be detected) the oven was turned off and full vacuum was applied to remove any residual solvents (overnight).
  The dried coated tri-calcium phosphate powder was transferred into light protected vial and stored at 4° C.
  Drug release profile: the coated substrate was hydrated (5% serum at 37° C.) and the release of doxycycline from the tri-calcium phosphate particles impregnated/coated with the matrix composition was followed and quantified by HPLC. The release profile is presented in FIG. 1.

Example 2—Drug Release from PVA Particles Impregnated/Coated with the Sustained Release Formulation of the Invention Coated/impregnated PVA particles were prepared as described above in Example 1. Following hydration (5% serum at 37° C.) the release of doxycycline from the PVA particles impregnated/coated with the matrix composition was detected and quantified by HPLC. The release profile is presented in FIG. 2.

Figure 2:
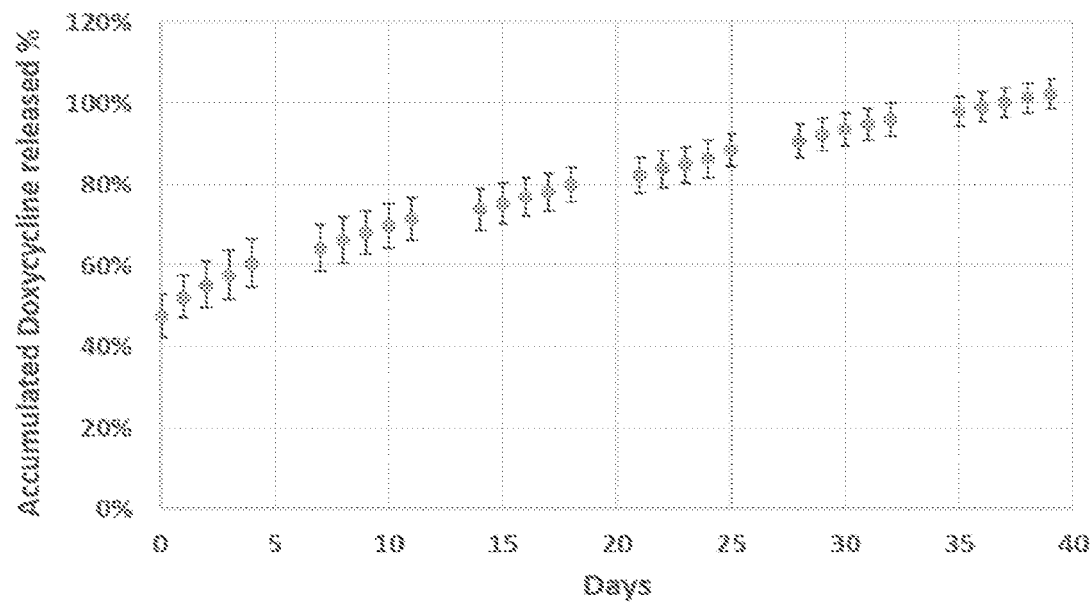
FIG. 2 shows the accumulated release profile of doxycycline hyclate from hydrated (5% serum at 37° C.) poly vinyl alcohol (PVA) particles impregnated with a matrix composition composed of PLGA, cholesterol, DPPC, DSPC and doxycycline hyclate, post hydration in 5% serum at 37° C.

As can be seen in FIG. 2, the first hour release reached about 45% of the doxycycline in the coating matrix. Further investigation the first hour release revealed that when the collected sample was centrifuged (spin-down) and further sieved (45 um filter) or vice versa (sieved and further centrifuged), the amount of the doxycycline released within the first hour and detected by HPLC was lower by at least 50% (e.g. ~20%). Without being bound by theory or mechanism of action, it is estimated that the collected sample (before centrifuging and/or filtering the collected sample) includes apart from doxycycline molecules that were release from the formulation, also small fragments of coated PVA particles.

Coated and uncoated PVA particles were further analyzed by FTIR and SEM.

No indications to interaction between the PVA particles and the coating matrix were found by FTIR.

Figure 3A:
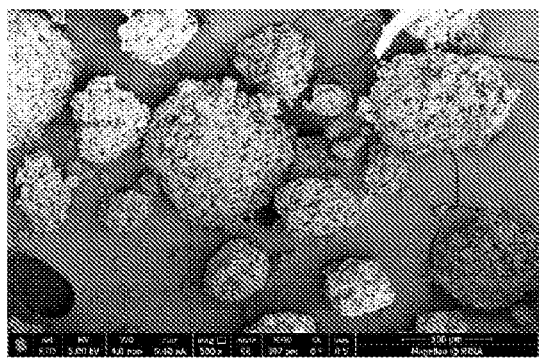
FIGS. 3A, 3B, 3C and 3D show SEM images of uncoated globular PVA particles having a porous rough terrain surface (FIGS. 3A and 3B, magnification ×500 and ×25000 respectively), and similar PVA particles impregnated with a matrix composition composed of PLGA, cholesterol, DPPC, DSPC and doxycycline hyclate (FIGS. 3C and 3D, magnification ×500 and ×25000 respectively).
Figure 3B:
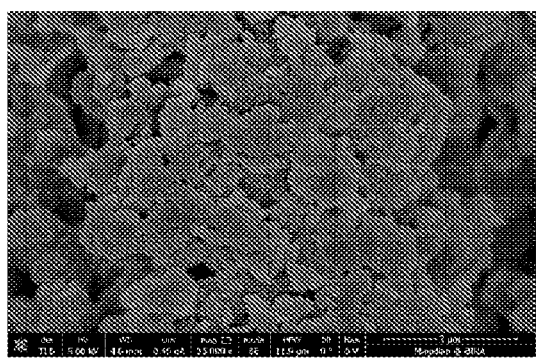
Figure 3C:
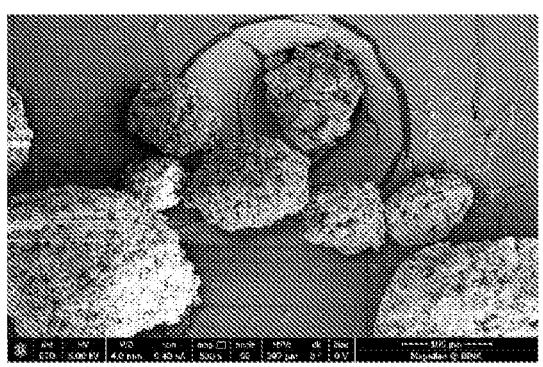
Figure 3D:
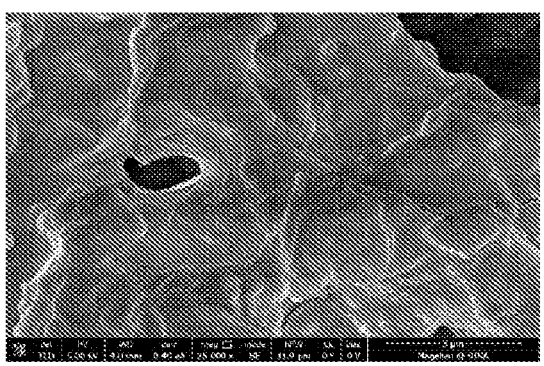

SEM images of uncoated PVA particles disclose globular particles having a porous rough terrain surface (FIGS. 3A and 3B). Images of coated PVA show that both outer and inner surfaces of the particles are coated (FIGS. 3C and 3D).

Without wishing to be bound by theory or mechanism of action, the use of PVA may be advantageous due to the fact that it is dissolved soon after the coating matrix comprising the drug is disintegrated. Exposure of the PVA to body fluids will initiate its degradation and removal, leaving no traces at the treated surgical site.

Example 3—Drug Release from Absorbable Gelatin Sponge Containing the Sustained Release Formulation of the Invention A 1 cm*1 cm piece of collagen sponge was placed in a 20 ml vial. 0.4 ml of solution AB (as described above in Example 1) were added to the vial and the vial was left closed at room temperature for 10 min. The piece of collagen sponge impregnated with solution AB was transferred to a 4 ml vial for evaporation of the solvents followed by vacuum overnight. This collagen piece was put to release experiment.

Following hydration (5% serum at 37° C.) the release of doxycycline from the gelatin sponge piece impregnated with the matrix composition into the surrounding was detected and quantified by HPLC.

Example 4—Pre-Clinical Testing of TCP Granules Coated/Impregnated with a Matrix Composition According to Embodiments of the Present Invention for the Treatment of Intramuscular Surgical Site Infection The objective of this study is to assess the efficacy of tri-calcium phosphate granules (~100 μm) coated with a matrix composition comprising doxycycline according to some embodiments of the invention ("Test article") in reducing bacterial proliferation following induction of a surgical site infection (SSI) model attained by intramuscular implantation of the Test article combined with *Staphylococcus aureus* (ATCC 25923) in SD rats. The preparation of the "test article" is described in Example 1.

All preclinical testing is performed in accordance with the guidelines for Regulation of Animal Experiments in the State of Israel and according to the Ethics Committee of the research institution.

Animal Model:
Sprague Dawley®™ SD®™ male rats, 11-12 weeks of age.

Bacterial Inoculum:
*Staphylococcus aureus* from ATCC 25923 source, provided in a ready to use state divided to two respective concentrations of $1 \times 10^7$ and $1 \times 10^8$ CFU/ml.

Test Material:
Synthetic tri-calcium phosphate (TCP)—50-100 μm CamBioceramic granules coated with a matrix composition comprising doxycycline as described in Example 1, provided as a "ready to use" powder. Prior to surgical procedure, Vehicle Material is aseptically divided into aliquots of 50±2 mg placed in glass vials (one aliquot per implantation site).

Constitution of Tests Groups & Doses:
Table 1 below lists the experimental groups comprised in the study:

TABLE 1

| Group No. | No. of Animals | Bacterial Inoculum S. aureus (ATCC 25953) Suspension Concentration (CFU/ml) | S. aureus (ATCC 25923) Implanted Volume (μl) | Implanted Material | Implanted Volume (mg) | Route of Implantation | Proposed Observation Period (days post implantation) |
|---|---|---|---|---|---|---|---|
| 1 | n = 2 | | | Untreated | | | 14 |
| 2 | n = 6 | $1 \times 10^7$ | 50 | TCP test-article | 50 | Implantation into an intramuscular pocket formed in the right gluteal muscle | |
| 3 | n = 6 | | | test-article | | | |
| 4 | n = 6 | $1 \times 10^8$ | 50 | TCP test-article | 50 | | |
| 5 | n = 6 | | | test-article | | | |

Test Procedures:
Pre-Surgery Preparations: Animals are administered an opioid analgesic (Buprenorphine at a dose level of ~0.075 mg/kg) by subcutaneous injection approximately 1-2 hours prior to surgical procedure. In all cases, animals are subjected to general anesthesia by Isofluran inhalation (2-4% in oxygen at a flow of 0.8-1.2 L/min.).

Implantation of Test Materials into an intramuscular pocket is performed in each animal (excluding untreated animals) under aseptic conditions as follows:

Animal is placed on a heated surface in prone position. A longitudinal skin incision is performed at the dorsal lumbar area, approximately 2 cm right to the vertebral column and extended until visualization of the gluteal muscles is obtained. A pocket measures approximately 2 cm in length and 1 cm in depth is formed in the gluteal muscles using blunt dissection technique or a surgical blade.

The Test Material is poured into the pocket directly from the weighing paper while retracting the pocket's edges with forceps. Subsequently and while the pocket's edges are still retracted, 50 μl of the bacterial suspension (at the respective concentration) or physiological saline (in control sample) is administered into the formed pocket using pipette. The musculature and skin are closed by simple interrupted sutures using appropriate suture materials and surgical clips, respectively.

The closed incision is cleaned of blood residuals by rinsing it with physiological saline then applied with Polydine solution.

Post-Operative Care: Animals are administered subcutaneously with buprenorphine at a dose of ~0.075 mg/kg twice daily for up to 3 days post-surgery.

Observations and Examinations: Duration—~14 days. Clinical signs and body weight are monitored. Incision sites are inspected and evaluated once daily. Additionally, in order to assess a local reaction in deeper tissues, sites of surgery are subjected to manual palpation and graded according to a 5-grade scale as follows: 0=no palpable nodule, 1=barely palpable nodule, 2=nodule 0.25-0.5 cm in diameter, 3—nodule>0.5 cm in diameter, 4=abscess expressed.

The entire implantation site area of all animals, is harvested, weighted and individually placed in a labeled vial filled with 10 ml of physiological saline. Vials are placed on ice until performance of microbiological assay.

Quantitation of Bacteria in Tissue:
Each test site is aseptically cut into small pieces using sterile scissors, thus exposing the contents of the pocket.

Suspension of minced tissue in saline is vortexed for 1 min.

10-fold dilutions of suspension in saline are prepared (up to 10-5 for the highest inoculum size).

Specimens are then plated on selective agar and on blood agar. Following incubation at 37° C. for 24-48 hours, the number of bacteria recovered is quantified in each medium and expressed as colony forming units per sample.

Figure 4:
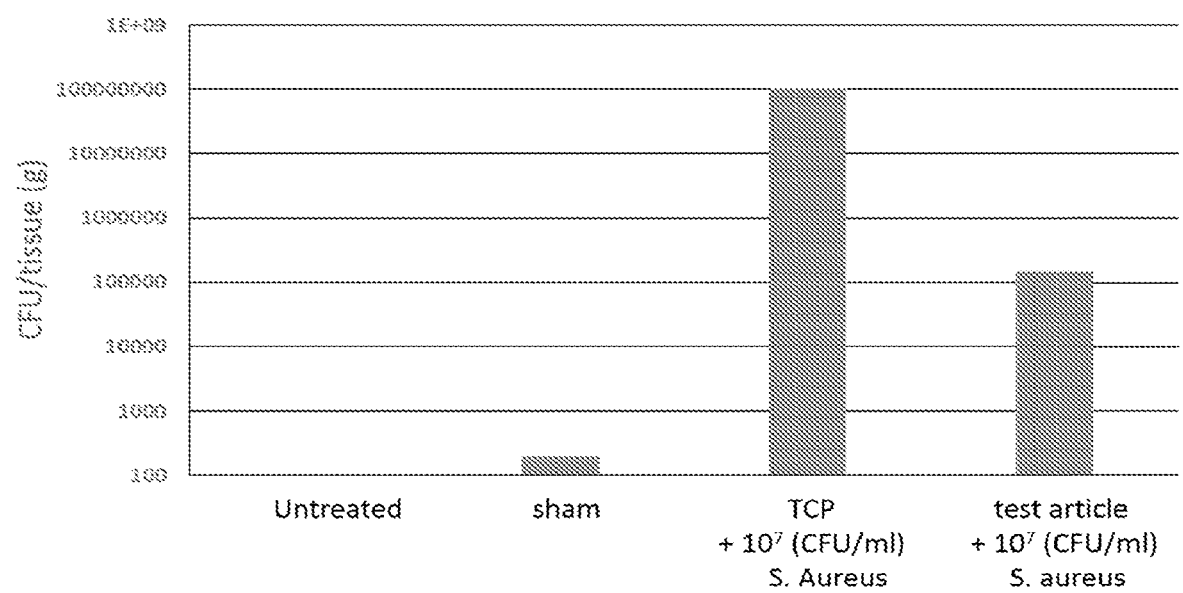
FIG. 4 shows the efficacy of tri-calcium phosphate granules (~100 μm) coated with a matrix composition comprising doxycycline according to some embodiments of the invention ("Test article") in reducing bacterial proliferation following induction of a surgical site infection (SSI) model attained by intramuscular implantation of the Test article combined with *Staphylococcus aureus* in SD rats. Implantation of uncoated TCP particles combined with *Staphylococcus aureus* served as control.

The efficacy assessment results are presented in the following Table 2 and summarized in FIG. 4.

material/bacterial colonies, 3=Multiple large foci of residual material/bacterial colonies, 4=Abundant residual material/bacterial colonies filling the surgical site.

Results: Macroscopic Evaluation of Test Sites at Necropsy:

In general, in almost all animals assigned to both TCP treated groups (i.e. groups no. 2 & 4), a bulge measures 0.5-2 cm in diameter was observed at the center of the Test Site. Additionally, in few of the Test Sites of groups 2 & 4, adhesion of the skin to the inner tissue was noted.

TABLE 2

| | | Treatment | | | |
|---|---|---|---|---|---|
| | | *S. aureus* (ATCC 25923) Suspension | | Quantification of Bacteria in Samples | |
| Animal No. | Implanted Material | concentration (CFU/ml) | Route of Implantation | CFU/sample | CFU/gr. of sample |
| 1 | | UNTREATED | | 150 | 44 |
| 2 | | | | 150 | 38 |
| 1 | TCP | NOT INDUCED | Implantation into | 650 | 89 |
| 2 | (Group 1) | (sham) | an intramuscular | 1500 | 313 |
| 3 | TCP | $1 \times 10^7$ | pocket formed in | 316000 | 43288 |
| 4 | (Group 2) | | the right gluteal | 310000000 | 62000000 |
| 5 | | | muscle | 280000000 | 42424242 |
| 6 | | | | 1830000000 | 338888889 |
| 8 | | | | 660000000 | 146666667 |
| 9 | test article | $1 \times 10^7$ | | 800000 | 150943 |
| 10 | (Group 3) | | | 79000 | 17174 |
| 12 | | | | 1150000 | 396552 |
| 13 | | | | 1300000 | 265306 |
| 14 | | | | 142000 | 33023 |
| 15 | TCP | $1 \times 10^8$ | | 8950000 | 2355263 |
| 16 | (Group 4) | | | 243000 | 65676 |
| 17 | | | | 24500 | 3356 |
| 20 | | | | 2470000000 | 475000000 |
| 21 | test article | $1 \times 10^8$ | | 77000 | 17907 |
| 22 | (Group 5) | | | 182000 | 49189 |
| 24 | | | | 2000000 | 263158 |
| 25 | | | | 35500 | 8452 |
| 26 | | | | 306000 | 62449 |

Conclusion: The results obtained in this study, including macroscopic observations, microbiological assay and histopathological evaluation, clearly indicate that a substrate (e.g. Synthetic tri-calcium phosphate) coated with formulation containing doxycycline has significantly reduced bacterial proliferation in an intramuscular surgical site infection (SSI) model in SD rats.

Histopathology—14 days post-surgical procedure, animals were sacrificed and the entire implantation site area was macroscopically evaluated for the degree of inflammatory reaction. Animals #7, 11, 18 & 23 of groups #. 2, 3, 4 & 5, respectively, were then harvested, weighed and sent for microbiological evaluation towards quantification of the bacteria in the samples.

Slides Preparation: histological processing performed as follows: Each sample was decalcified, trimmed, embedded in paraffin and 3 sections, each approximately at 5 micron thickness, interspaced at about 500 micron from each other were performed. Each of the 3 slides was stained with Hematoxylin & Eosin (H&E).

Histopathological Evaluation: The amount of residual implanted material and presence of bacterial colonies were evaluated and scored according to the following grading scale: 0=No residual implant/bacterial colonies observed, 1=One or two small foci of material/bacterial colonies, 2=Multiple small, with or without a large focus of residual In contrast, only a low rise of in the tissue was detected in the Test Sites of 2 out of 6 and 1 out of 6 animals assigned to groups no. 3 & 5, respectively.

Histopathological Findings:

Animal #7 and #18 of Groups 2 and 4 respectively—TCP combined with $1 \times 10^7$ or $1 \times 10^8$ CFU/ml of Bacteria: The intramuscular pocket in the gluteal muscle contained collections of polymorphonuclear cell (abscess formation), necrosis and Vehicle Item (TCP) granules surrounded by granulomatous (i.e., macrophages, giant cells) reaction. The entire reactive site is surrounded by early maturing capsular reaction. Numerous bacterial colonies are also identified, closely and within the abscesses. The abscess formation is scored grade 3.

Animal #11 and #23 of Groups 3 and 5 respectively—"test article" combined with $1 \times 10^7$ or $1 \times 10^8$ CFU/ml of Bacteria: The intramuscular pocket in the gluteal muscle contained collections of Tri Calcium Phosphate (TCP) granules (which is one of the components of the implanted Test Device) surrounded by granulomatous (i.e., macrophages, giant cells) reaction, and sporadic minimal (grade 1) mononuclear cell infiltration, indicative of excellent potential in reducing bacterial proliferation.

Conclusion: Samples of groups 2 and 4 (implantation of TCP only): The intramuscular pocket in the gluteal muscle contained abscess formation, associated with Vehicle Item (TCP) granules and presence of numerous bacterial species. There are no apparent differences in any of the components and/or scores when comparing the reactions seen in samples from groups 2 and 4.

Samples of groups 3 and 5 ('test article"): The intramuscular pocket in the gluteal muscle contained collections of Tri Calcium Phosphate (TCP) granules surrounded by granulomatous (i.e., macrophages, giant cells) reaction, and sporadic minimal mononuclear cell infiltration, indicative of excellent potential in reducing bacterial proliferation. There are no apparent differences in any of the components and/or scores when comparing the reactions seen in samples from groups 3 and 5. It can be concluded that the test compound was highly effective in reducing proliferation of bacteria at the surgical site.

Example 5—Eradication of an Established Biofilm in the Presence of TCP Particles Coated with a Matrix Composition According to Some Embodiments of the Invention The effectiveness of tri-calcium phosphate granules coated with a matrix composition according to embodiments of the invention in eradicating established biofilm was measured using the MBEC™ (Minimum Biofilm Eradication Concentration) Physiology and Genetics Assay.

MBEC™ Test Method Overview: MBEC™ test method specifies the operational parameters required to grow and treat different bacterial biofilms in a high throughput screening assay. The assay device consists of a plastic lid with ninety-six (96) pegs and a corresponding receiver plate with ninety-six (96) individual wells that have a maximum 200 µL working volume. Biofilm is established on the pegs in a batch culture based model (i.e., no flow of nutrients into or out of an individual well) with gentle mixing. The established biofilm is transferred to a new receiver plate for disinfectant efficacy testing.

Sample Description:

Each sample set tested included the following groups listed in the table 3 below:

Test Organisms: *Staphylococcus aureus* (an osteomyelitis-related strains); source: ATCC 29213; Dilution/Challenge Media: 1,000×TSB+10% human serum 24 hrs; Growth Media/agar: Tryptic Soy Broth/Tryptic Soy agar for 24 hrs Aerobic cond.

TEST METHOD overview: The experimental process for high-throughput antimicrobial susceptibility testing using the hydroxyapatite coated MBEC™ P&G assay. This standard protocol was broken into a series of small steps, each of which is detailed in the sections below.

1. Culture/Inoculum Preparation:

Using a cryogenic stock (at −70° C.), a first sub-culture of *Staphylococcus aureus* was streaked out on OSA (organism specific agar). The plates were incubated at appropriate growth conditions for 20±2.0 hours and further stored at 4° C.

A second sub-culture taken from the first sub-culture was streaked out on OSA. The plates were incubated at appropriate growth conditions for 20±2.0 hours. An isolated colony from the second sub-culture was aseptically removed from the OSA plate and inoculated into 50 mL of sterile bacterial liquid growth broth, followed by incubation appropriate growth conditions for 20±2.0 hours (at 150 rpm).

The inoculum was adjusted to an approximate cell density of $10^6$ CFU/mL.

Samples (100 µL) of the diluted organism were used for an inoculum check by serially diluting and spot plating on OSA in triplicate.

Preparation of the Challenge Plate:

150 µL of the remaining diluted organism were placed in each of the corresponding wells of an MBEC™ P&G device except the sterility controls (Table 5). The device was placed on an orbital shaker (110 RPM) in a humidified incubator at 37±1° C.

Sample Sterility Controls:

Pegs were broken from BGCH wells with flamed pliers. Each peg was placed into 200 µL of the neutralizer. The pegs were sonicated for 30 minutes. The recovery suspension was then serially diluted and spot plated on OSA. This served as a biofilm growth check.

200 µL of sterile TSB was added to wells GC and SC-M of the challenge plate, respectively. These served as sterility

TABLE 3

| Code | Sample | Description | Contact time | Concentrations |
|---|---|---|---|---|
| A | β-TCP | β-Tri Calcium Phosphate (β-TCP) | 24 ± 2 hrs | 0.3%, 1%, 3%, 10%, & 30% w/v (mg/µl) so in 200 µl, there is 0.6, 2, 6, 20 and 60 mg of the sample, respectively |
| B | Test-article | Test article formulation: β-TCP granules coated/impregnated with a matrix composition comprising doxycycline hyclate | 24 ± 2 hrs | 0.3%, 1%, 3%, 10%, & 30% w/v (mg/µl) so in 200 µL, there is 0.6, 2, 6, 20 and 60 mg of the sample, respectively |
| C | β-TCP + Doxycycline | Doxycycline hyclate non-formulated β-TRI Calcium Phosphate (β-TCP) and free (not formulated) doxycycline hyclate (10 mg/ml and 5 mg/ml solutions in distilled water). | 24 ± 2 hrs | 0.3%, 1%, 3%, 10%, & 30% w/v (mg/µl) so in 200 µL, there is 0.06 at 3%, 0.06 at 3%, .06 2, 6, 20 and 60 mg of TCP, respectively that should be impregnated with 6.72, 22.4, 67.2, 224 and 672 µg of the doxycycline, respectively | control (SC) and growth control (GC) for each trial of each organism. BGCh is the biofilm Growth Check. N wells are the neutraliser toxicity controls and N:50 wells are the neutraliser efficacy controls.

TABLE 4

Challenge plate

|   | β-TCP | | | Test-article | | | β-TCP + Free Doxycycline | | | Gentamicin | | |
|---|---|---|---|---|---|---|---|---|---|---|---|---|
| A | A 30% | A 30% | A 30% | B 30% | B 30% | B 30% | C 30% | C 30% | C 30% | 32 | 32 | 32 |
| B | A 10% | A 10% | A 10% | B 10% | B 10% | B 10% | C 10% | C 10% | C 10% | 16 | 16 | 16 |
| C | A 3.0% | A 3.0% | A 3.0% | B 3.0% | B 3.0% | B 3.0% | C 3.0% | C 3.0% | C 3.0% | 8.0 | 8.0 | 8.0 |
| D | A 1.0% | A 1.0% | A 1.0% | B 1.0% | B 1.0% | B 1.0% | C 1.0% | C 1.0% | C 1.0% | 4.0 | 4.0 | 4.0 |
| E | A 0.3% | A 0.3% | A 0.3% | B 0.3% | B 0.3% | B 0.3% | C 0.3% | C 0.3% | C 0.3% | 2.0 | 2.0 | 2.0 |
| F | SC-A | SC-A | SC-A | SC-B | SC-B | SC-B | A 0.3% (0.06 μg Dox) | A 0.3% (0.06 μg Dox) | A 0.3% (0.06 μg Dox) | 1.0 | 1.0 | 1.0 |
| G | N:50 | N:50 | N:50 | N | N | N | SC-C | SC-C | SC-C | A 0.3% (0.06 μg Dox) | A 0.3% (0.06 μg Dox) | A 0.3% (0.06 μg Dox) |
| H | BGCh | BGCh | BGCh | SC | SC | SC | GC | GC | GC | GC | GC | GC |

Using a sterile 96-well microtitre plate the following was done aseptically to set up the challenge plates listed in Table 4:

Neutralization control: 200 μL of the neutralizer were added to 300 μg of the doxycycline in the N:50 wells (final concentration of Doxycycline in D/E (neutralizer) is 1.5 mg/mL).

Neutralizer toxicity control: 200 μL of the neutralizer was added to N wells.

Biocide sterility control: 60 mg of β-TCP, test article and β-TCP+Doxycycline were added to SC A-C wells.

Antimicrobial Challenge for Preformed Biofilm:

The biofilm formed on the lid of the MBEC device was rinsed by dipping the lid into saline (~30 seconds) to remove planktonic cells. The lid was then put on top of the challenge plate and incubated on a rotary shaker at 110 rpm at 35±2° C. for 24±2 hours.

Biofilm Recovery:

After incubation (specified above), planktonic cells were rinsed off the biofilm by dipping the lid into saline (~20-30 seconds). The lid was then transferred to a neutralizer/recovery plate and put in a sonicator (~30 minutes) to dislodge surviving biofilm.

Determination of Planktonic MBC:

20 μL from each well of the challenge plate were removed, and placed into the corresponding wells of a fresh 96 well plate containing 180 μL DE neutralizer. The plate was incubated at 35±2° C. for 24±2 hours. MBC results were visually determined post incubation.

$LOG_{10}$ Reduction:

Following sonication, 100 μL from each well of the MBEC™ plate, were put into the first 12 empty wells of the first row of a 96 well-micro titer plate and were further diluted by 10 fold down each of the 8 rows ($10^0$-$10^7$ dilution). 5 μL from each well were then used for spotting prepared OSA plates. The agar plates were incubated at 37±1° C. and counted after approximately 24-48 hours of incubation. The arithmetic mean of the number of colonies counted on the plates was calculated.

100 μL of the sterile neutralizer was added to each well of the recovery plate to top up the volume back to 200 μL. The refilled plate is incubated at 35±2° C. for 24±2 hours.

Comparator MBEC results were determined following the 24±2 hour incubation using the plate reader.

The log density for one peg was calculated as follows:

$LOG_{10}(CFU/peg)=LOG_{10}[(X/B)(D)]$ where: X=mean CFU; B=volume plated (0.02 mL) and D=dilution.

The overall biofilm accumulation was determined by calculating the mean of the log densities calculated.

$LOG_{10}$ reduction for each dilution was calculated as follows: $LOG_{10}$ Reduction=Mean $LOG_{10}$ Growth Control−Mean $LOG_{10}$ Test Sample.

Results:

Average $LOG_{10}$ CFU/peg recoveries are presented in Table 5:

TABLE 5

Average Log10 CFU/peg recoveries

|  | 1 | 2 | 3 | Average | St. Dev |
|---|---|---|---|---|---|
| A |  |  |  |  |  |
| 30.0% | 3.90 | 3.60 | 3.60 | 3.70 | 0.17 |
| 10.0% | 3.60 | 3.90 | 3.60 | 3.70 | 0.17 |
| 3.0% | 3.60 | 3.78 | 3.60 | 3.66 | 0.10 |
| 1.0% | 3.60 | 3.60 | 3.90 | 3.70 | 0.17 |
| 0.3% | 3.90 | 3.90 | 3.60 | 3.80 | 0.17 |
| B |  |  |  |  |  |
| 30.0% | 0.00 | 0.00 | 0.00 | 0.00 | 0.00 |
| 10.0% | 0.00 | 0.00 | 0.00 | 0.00 | 0.00 |
| 3.0% | 0.00 | 0.00 | 0.00 | 0.00 | 0.00 |

TABLE 5-continued

Average Log10 CFU/peg recoveries

| | 1 | 2 | 3 | Average | St. Dev |
|---|---|---|---|---|---|
| 1.0% | 1.91 | 2.45 | 0.00 | 1.45 | 1.29 |
| 0.3% | 2.08 | 3.30 | 3.08 | 2.82 | 0.65 |
| C | | | | | |
| 30.0% | 0.00 | 0.00 | 0.00 | 0.00 | 0.00 |
| 10.0% | 0.00 | 0.00 | 0.00 | 0.00 | 0.00 |
| 3.0% | 2.90 | 3.20 | 3.08 | 3.06 | 0.15 |
| 1.0% | 3.60 | 3.60 | 3.90 | 3.70 | 0.17 |
| 0.3% | 2.90 | 3.60 | 3.56 | 3.35 | 0.39 |
| D (µg) | | | | | |
| 32 | 0.00 | 0.00 | 0.00 | 0.00 | 0.00 |
| 16 | 0.00 | 0.00 | 0.00 | 0.00 | 0.00 |
| 8.0 | 0.00 | 0.00 | 0.00 | 0.00 | 0.00 |
| 4.0 | 1.61 | 2.30 | 0.00 | 1.31 | 1.18 |
| 2.0 | 2.30 | 0.00 | 2.78 | 1.69 | 1.49 |
| 1.0 | 4.72 | 2.60 | 2.30 | 3.21 | 1.32 |
| 0.5 | 3.90 | 2.90 | 3.64 | 3.48 | 0.52 |

TABLE 6

Log Reductions

| Log Reduction | | | % Comp. | Log R | T-test | S/NS |
|---|---|---|---|---|---|---|
| A | Vs. | B | 30.0% | 3.70 | 0.00 | S |
| | | | 10.0% | 3.70 | 0.00 | S |
| | | | 3.0% | 3.66 | 0.00 | S |
| | | | 1.0% | 2.25 | 0.02 | S |
| | | | 0.3% | 0.98 | 0.03 | S |
| A | Vs. | C | 30.0% | 3.70 | 0.00 | S |
| | | | 10.0% | 3.70 | 0.00 | S |
| | | | 3.0% | 0.60 | 0.00 | S |
| | | | 1.0% | 0.00 | 0.50 | NS |
| | | | 0.3% | 0.45 | 0.07 | NS |
| GC | Vs. | D | 32 | 4.59 | 0.00 | S |
| | | | 16 | 4.59 | 0.00 | S |
| | | | 8.0 | 4.59 | 0.00 | S |
| | | | 4.0 | 3.29 | 0.00 | S |
| | | | 2.0 | 2.90 | 0.00 | S |
| | | | 1.0 | 1.38 | 0.02 | S |
| | | | 0.5 | 1.11 | 0.00 | S |

MBC and MBEC Visual Reading data is presented in Table 7

TABLE 7

MBC and MBEC Visual Reading data

| MBEC | 1 | 2 | 3 | 4 | 5 | 6 | 7 | 8 | 9 | 10 | 11 | 12 |
|---|---|---|---|---|---|---|---|---|---|---|---|---|
| A | + | + | + | - | - | - | - | - | - | - | - | - |
| B | + | + | + | - | - | - | - | - | - | - | - | - |
| C | + | + | + | - | - | - | + | + | + | - | + | - |
| D | + | + | + | - | - | - | + | + | + | + | + | + |
| E | + | + | + | + | + | + | + | + | + | + | + | + |
| F | - | - | - | - | - | - | + | + | + | + | + | + |
| G | + | + | + | + | + | + | - | - | - | + | + | + |
| H | - | - | - | - | - | - | + | + | + | + | + | + |
| MBC | 1 | 2 | 3 | 4 | 5 | 6 | 7 | 8 | 9 | 10 | 11 | 12 |
| A | + | + | + | - | - | - | - | - | - | - | - | - |
| B | + | + | + | - | - | - | - | - | - | - | - | - |
| C | + | + | + | - | - | - | - | - | - | - | - | - |
| D | + | + | + | - | - | - | - | - | - | - | + | + |
| E | + | + | + | - | - | - | - | - | - | - | + | + |
| F | - | - | - | - | - | - | - | - | - | - | + | + |
| G | + | + | + | + | + | + | - | - | - | + | + | + |
| H | - | - | + | - | - | - | + | + | + | + | + | + |

Conclusion: The log reduction data indicated that the test article (TCP granules coated with a matrix composition according to embodiments of the invention) managed to kill a preformed biofilm at a minimum concentration of 3.0% and was effective even at 1.0% (>99% kill). In contrast, the non-formulated doxycycline with β-TCP was effective at concentrations of 10% or above.

Example 6—Inhibition of Biofilm Formation in the Presence in the Presence of TCP Particles Coated with a Matrix Composition According to Some Embodiments of the Invention The effectiveness of tri-calcium phosphate granules coated with a matrix composition according to embodiments of the invention in inhibiting biofilm formation was evaluated by calculating the bacterial log reduction values using the MBEC™ (Minimum Biofilm Eradication Concentration) Physiology and Genetics Assay (The system is described above in Example 5).

Culture/Inoculum preparation followed the procedure described above in Example 5. Preparation of the Challenge plate:

TABLE 8

Staphylococcus aureus

| A | SC-A | SC-A | SC-A | B1 | B1 | B1 | A1 | A1 | A1 |
|---|---|---|---|---|---|---|---|---|---|
| B | SC-B | SC-B | SC-B | B2 | B2 | B2 | A2 | A2 | A2 |
| C | N:50 | N:50 | N:50 | B3 | B3 | B3 | A3 | A3 | A3 |
| D | N | N | N | B4 | B4 | B4 | A4 | A4 | A4 |
| E | | | | B5 | B5 | B5 | A5 | A5 | A5 |
| F | | | | | | | | | |
| G | | | | | | | | | |
| H | BGCh | BGCh | BGCh | | | | | | |

Challenge plate design: SC wells are sterility controls for each experiment.
GC is the growth control.
BGCh is the biofilm Growth Check.
N wells are the neutralizer toxicity controls.
N:50 wells are the efficacy controls.

Using a sterile 96-well microtitre plate the following was done aseptically to set up the above challenge plates:

Efficacy control: 150 µL of the neutralizer was added to 672 µg of the doxycycline in the N: 50 wells (final concentration of Doxycycline in D/E was 4.48 mg/mL).

Neutralizer toxicity control: 150 µL of the neutralizer was added to N wells.

Biocide sterility control: 60 mg of the test-article were added to SC wells.

60 mg of each of TCP and test-article were added as in the layout of Table 8 in columns 1-9 (n=3). 150 µL of the inoculated media were added to each well of the biofilm formation/challenge 96 well plate except for the sterility controls.

Antimicrobial Challenge for Biofilm Formation Inhibition:

The lid was transferred to the challenge plate and incubated on a rotary shaker at 110 rpm at 35±2° C. for 24±2 hours. Planktonic cells were rinsed from the biofilm that have formed on the lid of the MBEC device by dipping the lid into a rinse plate (200 µL of saline per well) for 30 seconds. After the specified contact time, the MBEC™ lid was transferred to the neutralizer plate (200 µL of neutralizer per well).

The plate was placed in the sonicator and sonicated for 30 minutes to dislodge surviving biofilm.

Determination of planktonic MBC and $LOG_{10}$ Reduction were done as described above in Example 5.

Average $LOG_{10}$ recovery is summarized in Table 9 below.

TABLE 9

Average $LOG_{10}$ recovery

| | 1 | 2 | 3 | Average | StDev |
|---|---|---|---|---|---|
| A | | | | | |
| 30.0% | 4.60 | 5.38 | 4.90 | 4.96 | 0.39 |
| 10.0% | 5.30 | 5.56 | 5.45 | 5.43 | 0.13 |
| 3.0% | 4.90 | 5.30 | 5.08 | 5.09 | 0.20 |
| 1.0% | 5.38 | 5.51 | 5.60 | 5.50 | 0.11 |
| 0.3% | 5.60 | 5.20 | 5.60 | 5.57 | 0.23 |
| B | | | | | |
| 30.0% | 0.00 | 0.00 | 0.00 | 0.00 | 0.00 |
| 10.0% | 0.00 | 0.00 | 0.00 | 0.00 | 0.00 |
| 3.0% | 0.00 | 0.00 | 0.00 | 0.00 | 0.00 |
| 1.0% | 0.00 | 0.00 | 0.00 | 0.00 | 0.00 |
| 0.3% | 0.00 | 0.00 | 0.00 | 0.00 | 0.00 |

Log Reductions are presented in Table 10

TABLE 10

$LOG_{10}$ reduction

| Log Reduction | | % Comp. | LogR | Ttest | S/NS |
|---|---|---|---|---|---|
| A Vs. | B | 30.0% | 4.96 | 0.00 | S |
| | | 10.0% | 5.43 | 0.00 | S |
| | | 3.0% | 5.09 | 0.00 | S |
| | | 1.0% | 5.50 | 0.00 | S |
| | | 0.3% | 5.47 | 0.00 | S |

MBC and MBEC Visual Reading data is presented in Table 11:

TABLE 11

MBC and MBEC Visual Reading data

| MBC | 1 | 2 | 3 | 4 | 5 | 6 | 7 | 8 | 9 |
|---|---|---|---|---|---|---|---|---|---|
| A | - | - | - | - | - | - | + | + | + |
| B | - | - | - | - | - | - | + | + | + |
| C | - | - | - | - | - | - | + | + | + |
| D | + | + | + | - | - | - | + | + | + |
| E | + | + | + | - | - | - | + | + | + |
| F | | | | | | | | | |
| G | | | | | | | | | |
| H | | | | | | | | | |
| MBEC | 1 | 2 | 3 | 4 | 5 | 6 | 7 | 8 | 9 |
| A | - | - | - | - | - | - | + | + | + |
| B | - | - | - | - | - | - | + | + | + |
| C | - | - | - | - | - | - | + | + | + |
| D | + | + | + | - | - | - | + | + | + |
| E | + | + | + | - | - | - | + | + | + |
| F | | | | | | | | | |
| G | | | | | | | | | |
| H | + | + | + | | | | | | |

Conclusions: The A control compound (TCP only) had good recovery and growth over the duration of the challenge and at all tested concentrations of TCP.

The B test compound completely killed the bacteria that was inoculated into the test wells at every concentration tested. The MBC data indicated that all the cells were killed and simply inhibited at the tested concentrations.

Example 7—Pre-Clinical Testing of TCP Particles Coated/Impregnated with a Matrix Composition According to Embodiments of the Present Invention for the Treatment of Sternal Surgical Site Infection The objective of this study is to assess the efficacy of tri-calcium phosphate granules (~100 μm) coated with a matrix composition comprising doxycycline according to some embodiments of the invention ("Test article") in reducing bacterial proliferation following induction of a surgical site infection (SSI) model attained by sternal implantation of the Test article combined with *Staphylococcus aureus* (ATCC 25923) in New Zealand White rabbits. The preparation of the "test article" is described in Example 1.

Description:

A sternum defect in half sternum depth is performed on New Zealand White rabbits. 12 Female New Zealand White rabbits are randomly divided into two equal groups of 6 animals. They underwent median sternotomy with the application of either a "control article" (uncoated TCP) or "test article" (TCP particles coated/impregnated with matrix composition prepared as described in Example 1) mixed with a defined calibrated bacterial inoculum dose and are placed in the gap formed (e.g. sternum defect).

Rabbits are anesthetized using ketamine (30 mg/kg), xylazine (5 mg/kg) and atropine (1 to 3 mg/kg) intramusculary and maintained on isoflurane after intubation.

The sternotomy is performed using standard aseptic techniques. A sternum defect in half sternum depth is performed. Equal amounts of control article or test articles mixed separately with bacterial inoculum are applied to cover the cut bone surface, and the time to hemostasis is recorded. The sternum is surgically closed (sternal halves are secured with monofilament suture, and incision is closed in layers). Daily observations are performed for general health. Animals are sacrificed after 6 weeks. Each sternum is harvested for radiographic, histologic, hematologic and mechanical analysis to asses sternal healing.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treatment or prophylaxis of a soft-tissue incision site infection associated with a surgical operation, wherein the method comprises:
  administering directly to the soft-tissue incision site, a biodegradable mineral substrate shaped in the form of particles,
    wherein the mineral substrate is impregnated or has its surface coated fully or partially with a matrix composition,
      wherein the matrix composition comprises:
        (a) a biodegradable polyester;

(b) a first lipid component comprising at least one sterol, wherein the at least one sterol is non-covalently associated with the biodegradable polyester;
(c) a second lipid component comprising at least one phospholipid having fatty acid moieties of at least 12 carbons; and
(d) an antibiotic agent selected from the group consisting of:
doxycycline and doxycycline hyclate.

2. The method of claim 1, wherein the soft-tissue incision is associated with a surgical operation selected from the group consisting of orthopedic surgical operations, spine surgical operations, operations on a digestive system organ, gastric ulcer procedures, gastric cancer procedures, open gastric bypass, appendectomy, colectomy, cholecystectomy, vagotomy, open billary tract procedures, small intestine procedures, colorectal procedures, cardiac procedures, hernia repair, vascular procedures, caesarian, prostatectomy, obstetric and gynecologic surgical operations, head and neck cancer surgery, transplantation surgeries, neurosurgery and plastic surgeries.

3. The method according to claim 2, wherein the surgical operation is a surgical operation on a digestive system organ.

4. The method of claim 3, wherein the digestive organ is selected from the group consisting of: esophagus, stomach, small intestine, large intestine, rectum, colon, appendix, liver, pancreas, gallbladder, and any combination thereof.

5. The method of claim 2, wherein the surgical operation on a digestive system organ includes a procedure selected from the group consisting of open gastric bypass, appendectomy, colectomy, cholecystectomy, vagotomy, open billary tract procedures, small intestine procedures, gastric ulcer procedures, gastric cancer procedures, colorectal procedures, and any combination thereof.

6. The method according to claim 2, wherein the soft-tissue incision is associated with cardiac surgery procedures.

7. The method according to claim 1, wherein the mineral substrate is selected from the group consisting of hydroxyapatite, fluorapatite, oxyapatite, wollastonite, apatite/wollastonite glass ceramics, anorthite, calcium fluoride, calcium sulfate, calcium carbonate, tetracalcium phosphate, α-tricalcium phosphate (α-TCP), β-tricalcium phosphate (β-TCP), amorphous calcium phosphate, dicalcium phosphate, agrellite, devitrite, canasite, phlogopite, monetite, brushite, octocalcium phosphate, whitlockite, cordierite, berlinite, combeite, phosphoric acid crystals, disodium hydrogen phosphate, and any combination thereof.

8. The method according to claim 7, wherein the mineral substrate is β-TCP.

9. The method according to claim 1, wherein the mineral substrate comprises particles having an average particle size of less than 200 microns (μm).

10. The method according to claim 9, wherein the average particle size is from 50 μm to 150 μm.

11. The method according to claim 1, wherein a majority of the particles are spherical, spheroidal, or any combination thereof.

12. The method according to claim 1, wherein the matrix composition comprises a phospholipid selected from a phosphatidylcholine or a combination of phosphatidylcholines having fatty acid moieties having at least 14 carbons.

13. The method according to claim 12, wherein the phospholipid is a phosphatidylcholine or a combination of phosphatidylcholines having fatty acid moieties having 14-18 carbons.

14. The method according to claim 1, wherein the biodegradable polyester is selected from the group consisting of PLA (polylactic acid), PGA (poly glycolic acid) and PLGA (poly(lactic co glycolic acid)).

15. The method according to claim 1, wherein the matrix composition further comprises a pharmaceutically active agent selected from the group consisting of: an antibiotic agent, an antiseptic agent, an anti-inflammatory agent, antifungal agent and any combination thereof.

16. The method according to claim 1, wherein the at least one sterol in the matrix composition comprises a cholesterol.

17. The method according to claim 1, wherein when the coated or impregnated mineral substrate is maintained in an aqueous environment, the matrix composition provides sustained release of said antibiotic agent, wherein at least 30% of the antibiotic agent is released from the composition at zero-order kinetics.

18. The method according to claim 1, wherein the matrix composition comprises:
(a) 10-30% w/w of a biodegradable polyester by weight of the matrix composition;
(b) 5-30% w/w of a first lipid component by weight of the matrix composition;
(c) 40-75% w/w of a second lipid component by weight of the matrix composition; and
(d) 1-20% w/w of doxycycline or doxycycline hyclate, by weight of the matrix composition.

19. The method according to claim 1, wherein the coated biodegradable mineral substate comprises between about 60-90% (w/w) of biodegradable mineral substrate and 10-40% (w/w) of the matrix composition.

20. The method of claim 1, wherein the infection is caused by hospital acquired resistant bacteria.

21. The method of claim 20, wherein the hospital acquired resistant bacteria include Methicillin-resistant S. aureus (MRSA).

22. The method according to claim 1, wherein the coated mineral substrate is formulated as a paste prior to application of the coated mineral substrate to the soft-tissue incision site.

* * * * *